(12) United States Patent
Raslambekov

(10) Patent No.: US 11,833,007 B1
(45) Date of Patent: Dec. 5, 2023

(54) SYSTEM AND A METHOD FOR ADJUSTING AN ORTHODONTIC TREATMENT PLAN

(71) Applicant: Oxilio Ltd, Larnaca (CY)

(72) Inventor: Islam Khasanovich Raslambekov, Long Island City, NY (US)

(73) Assignee: Oxilio Ltd, Larnaca (CY)

( * ) Notice: Subject to any disclaimer, the term of this patent is extended or adjusted under 35 U.S.C. 154(b) by 0 days.

(21) Appl. No.: 18/135,975

(22) Filed: Apr. 18, 2023

(51) Int. Cl.
*A61C 7/00* (2006.01)
*A61C 13/34* (2006.01)
*G16H 20/40* (2018.01)
*G06T 19/20* (2011.01)

(52) U.S. Cl.
CPC .............. *A61C 7/002* (2013.01); *A61C 13/34* (2013.01); *G06T 19/20* (2013.01); *G16H 20/40* (2018.01); *G06T 2207/30036* (2013.01); *G06T 2219/2004* (2013.01)

(58) Field of Classification Search
None
See application file for complete search history.

(56) References Cited

U.S. PATENT DOCUMENTS

| | | | |
|---|---|---|---|
| 7,156,661 B2 * | 1/2007 | Choi | A61C 7/002 433/213 |
| 8,075,306 B2 | 12/2011 | Kitching et al. | |
| 8,591,225 B2 | 11/2013 | Wu et al. | |
| 10,695,147 B1 | 6/2020 | Raslambekov | |
| 10,856,954 B1 | 12/2020 | Raslambekov | |
| 10,950,061 B1 | 3/2021 | Raslambekov | |
| 10,993,782 B1 | 5/2021 | Raslambekov | |
| 11,259,897 B1 | 3/2022 | Raslambekov | |
| 11,553,989 B2 | 1/2023 | Wen | |
| 2009/0191502 A1 * | 7/2009 | Cao | A61C 7/08 433/24 |
| 2010/0151404 A1 * | 6/2010 | Wu | A61C 7/00 433/24 |
| 2014/0288894 A1 | 9/2014 | Chishti et al. | |
| 2018/0110589 A1 | 4/2018 | Gao | |
| 2018/0235437 A1 * | 8/2018 | Ozerov | G16H 50/50 |
| 2020/0253693 A1 | 8/2020 | Wen | |
| 2022/0211466 A1 | 7/2022 | Raslambekov | |
| 2023/0005593 A1 * | 1/2023 | Raslambekov | G16H 20/40 |

* cited by examiner

*Primary Examiner* — Robert Bader
(74) *Attorney, Agent, or Firm* — BCF LLP

(57) ABSTRACT

A method and apparatus for adjusting an orthodontic treatment plan are provided. The method comprises: acquiring an actual 3D digital model indicative of actual positions of subject's teeth at a given stage of a orthodontic treatment plan; acquiring a planned 3D digital model indicative of planned positions subject's teeth at the given stage of the orthodontic treatment plan; aligning, during a first process, each one of the subject's teeth in the actual 3D digital model and in the planned 3D digital model individually; aligning, during a second process, the subject's teeth in the actual 3D digital model and in the planned 3D digital model, as a whole; determining the deviation value between the actual and planned positions of the given tooth; and in response to the deviation value being greater than a predetermined threshold, adjusting the current treatment plan to minimize the deviation value associated therewith the given tooth.

20 Claims, 13 Drawing Sheets

SYSTEM AND A METHOD FOR ADJUSTING AN ORTHODONTIC TREATMENT PLAN

FIELD

The present technology relates broadly to orthodontic treatments; and more specifically, to methods and systems for adjusting a current orthodontic treatment plan for a subject.

BACKGROUND

Planning an orthodontic treatment for a subject's teeth typically includes determining, based, for example, on 3D digital models (such as 3D mesh) of the subject's teeth, forces to be applied thereto. These forces define displacements of the subject's teeth from their current position to desired positions, which can be associated with the alignment of the subject's teeth. Further, based on the so determined forces, configurations of orthodontic appliances (such as aligners) can be determined, according to which the appliances can then be produced and provided to the subject for implementation of the treatment.

Thus, during the implementation of the orthodontic treatment, which can comprise a number of steps (also referred to herein as "stages"), the orthodontic appliances are consecutively used to apply the determined forces to the subject's teeth causing movement thereof towards the desired positions.

In the course of orthodontic treatment, such as in a given step, it is possible for deviations to occur between the planned positions of the subject's teeth and their actual positions. An intuitive approach to resolving these deviations may include a complete re-determination of the orthodontic treatment plan. However, this approach may be very resource-intensive, as it may necessitate, for example, the acquisition of new intraoral images, the production of new casts, the removal of auxiliary orthodontic devices, such as attachments, and further redetermination of their positions.

Certain prior approaches have been proposed to tackle the above-identified technical problem.

United States Patent Application Publication No.: 2018/0110,589-A1, published on Apr. 26, 2018, assigned to Guidemia Technologies Inc., and entitled "ORTHODONTIC PROCESS WITH DYNAMIC PLANNING AND INCREMENTAL IMPLEMENTATION", discloses an orthodontic process phased into two or more sub-processes for repositioning a patient's teeth. In each sub-process, a complete treatment plan is established, but not all (i.e. only some) appliances in the plan are fabricated to move the teeth, out of the expectation that teeth movement may not completely follow the full course as planned. The entire orthodontic process is thus featured with dynamic planning and incremental implementation of the plans, to address ever-changing treatment profile.

U.S. Pat. No. 8,075,306, issued on Dec. 13, 2011, assigned to Align Technology Inc., and entitled "SYSTEM AND METHOD FOR DETECTING DEVIATIONS DURING THE COURSE OF AN ORTHODONTIC TREATMENT TO GRADUALLY REPOSITION TEETH", discloses method and system for detecting and correcting deviation during an orthodontic treatment plan. The method includes the steps of receiving an un-segmented current teeth image representing a patient's teeth after an orthodontic treatment plan has begun and before the plan ends for the patient; matching a previously segmented teeth model with the current teeth image; and generating at least one corrective stage to define an intermediate tooth arrangement, wherein the at least one corrective stage repositions a digital teeth image so that a prescribed tooth arrangement of the previously segmented teeth model can be used.

U.S. Pat. No. 11,553,989-B2, issued on Jan. 17, 2023, assigned to Ulab Systems Inc., and entitled "TOOTH MODELING SYSTEM", discloses systems and methods for treating teeth to correct for malocclusions. This may be accomplished by applying a series of labels to a digital dental model and applying a rolling ball process to identify tooth boundaries separating one tooth from a neighboring tooth and to also determine the crown/gum margin. The user may further assign regions to the dental model to indicate hard regions and soft regions. With the dental model labeled and defined, the user may then generate a treatment plan for moving the labeled and defined tooth or teeth relative to one another to correct for any malocclusions. Upon approval of the treatment plan, a series of 3D printed dental appliances or aligners to be worn in series by the patient may be fabricated to ultimately move the tooth or teeth to a desired position.

United States Patent Application Publication No.: 2022/0211,466-A1, published on Jul. 7, 2022, assigned to Arkimos Ltd., and entitled "SYSTEMS AND METHODS FOR DETERMINING A JAW CURVE", discloses a method, executable by a processor, for planning an orthodontic treatment for a patient including determining tooth movement. The method includes obtaining a tooth and gingiva mesh from image data associated with teeth and surrounding gingiva; selecting a primary tooth to be moved to a desired position; displacing a tooth mesh of the primary tooth by a basic step distance toward the desired position determined on a jaw curve obtained for the teeth of the patient; determining if the displaced primary tooth collides with at least one secondary tooth in the desired position; in response to collision, displacing a tooth mesh of the secondary tooth away from the tooth mesh of the primary tooth by the basic step distance; and repeating determination of tooth collisions and displacing tooth contours of colliding teeth until no teeth of the teeth of the patient collide.

United States Patent Application Publication No.: 2014/0288,894-A1, published on Sep. 25, 2014, assigned to Align Technology Inc., and entitled "CLINICIAN REVIEW OF AN ORTHODONTIC TREATMENT PLAN AND APPLIANCE", discloses a computer used to create a plan for repositioning an orthodontic patient's teeth. The computer receives an initial digital data set representing the patient's teeth at their initial positions and a final digital data set representing the teeth at their final positions. The computer then uses the data sets to generate treatment paths along which teeth will move from the initial positions to the final positions.

U.S. Pat. No. 8,591,225-B2, issued on Nov. 26, 2013, assigned to Align Technology Inc, and entitled "TOOTH MOVEMENT MEASUREMENT BY AUTOMATIC IMPRESSION MATCHING", discloses systems and methods for detecting deviations from an orthodontic treatment plan. One method includes receiving a tracking model, performing a matching step between individual teeth in a plan model and the tracking model, comparing the tracking model with the plan model, and detecting one or more positional differences.

It is desired to provide improved methods and systems for determining the orthodontic landmarks.

SUMMARY

Developers of the present technology have devised methods and systems for resolving the deviations between the actual and planned of the subject's teeth during the implementation of the orthodontic treatment.

More specifically, the present methods and systems, in at least some non-limiting embodiments, are directed to adjusting a current orthodontic treatment plan, including: (i) first, individual aligning of each of the subject's teeth in 3D digital models, respectively representative of the actual and planned positions of the subject's teeth in a given arch form at the given step of the treatment plan; and (ii) second, aligning the subject's teeth in the 3D digital models as a whole, that is, representations of the given arch form in its entirety. The developers have realised that the consecutive implementation of these steps allows for more efficient alignment of the 3D models of the subject's teeth.

Also, unlike the prior art approaches reviewed above that include using an Iterative Closest Point (ICP) algorithm for aligning the representations of the entire given arch form of the subject's teeth, the present methods include using an outlier algorithm, such as a RANdom SAmple Consensus (RANSAC) algorithm, which, after the first alignment process provides comparable alignment accuracy, and execution of which requires significantly less computational resources of a processor, than that of the ICP algorithm.

Additionally, during the second alignment process, in some non-limiting embodiments of the present technology, representations of the subject's teeth in the 3D digital models can be replaced by primitive objects, alignment of which, compared to the alignment of the representations of the subject's teeth themselves, can require even less computational resources of the processor during the execution of the present method.

Further, after aligning the subject's teeth in the 3D digital models, a deviation value between an actual and planned positions of at least one tooth can be determined; and the current orthodontic treatment plan can be adjusted accordingly to minimize this deviation value. By doing so, the present methods and systems may allow minimizing the deviations between the actual and planned positions of the subject's teeth, accumulated by the given step of the current orthodontic treatment plan, more efficiently, which may thus allow meeting the goals thereof and, in the meantime, saving computational power of the processor.

More specifically, in accordance with a first broad aspect of the present technology, there is provided a method of adjusting a current orthodontic treatment plan having been previously determined for a subject. The current orthodontic treatment plan includes an indication of a tooth trajectory of the given tooth towards a target position thereof. The adjusting comprises determining a deviation value between an actual position and a planned position of a given tooth of the subject at a given stage of the current orthodontic treatment plan. The method is executable by a processor. The method comprises: acquiring, by the processor, an actual 3D digital model including a representation of each one of the subject's teeth in actual positions thereof at the given stage of the current orthodontic treatment plan; acquiring, by the processor, an indication of the current orthodontic treatment plan; generating, by the processor, based on the current orthodontic treatment plan, a planned 3D digital model including a representation of each one of the subject's teeth in planned positions at the given stage of the current orthodontic treatment plan; aligning, by the processor, during a first alignment process, each one of the subject's teeth in the actual 3D digital model and in the planned 3D digital model individually, the aligning for the given tooth of the subject's teeth including: matching (i) a respective representation of the given tooth in the actual 3D digital model with (ii) the respective representation of the given tooth in the planned 3D digital model; aligning, by the processor, during a second alignment process following the first alignment process, the subject's teeth in the actual 3D digital model and in the planned 3D digital model, as a whole, the aligning including: obtaining, by the processor, for each one of the subject's teeth, a respective primitive object of a plurality of representative objects; replacing, by the processor, each one of the subject's teeth in the actual and planned 3D digital models with the respective primitive object; and determining, by the processor, using an outlier detection algorithm, a matching between the plurality of representative objects, as a whole, in the actual and planned 3D digital models; determining, by the processor, the deviation value between the actual and planned positions of the given tooth as a deviation value between positions of the respective primitive object in the actual and planned 3D digital models of the subject's teeth following the second alignment process; and in response to the deviation value being greater than a predetermined deviation threshold, adjusting the tooth trajectory of the given tooth to minimize the deviation value associated therewith by an end of the current orthodontic treatment plan.

In some implementations of the method, the method further comprises identifying the respective representations of the given tooth in the actual and planned 3D digital models based on an ordinal number of the given tooth within a respective arch form of the subject.

In some implementations of the method, the matching the respective representations of the given tooth in the actual and planned 3D digital models comprises: merging, by the processor, instances of a reference point associated with the given tooth in the respective representations thereof in the actual and planned 3D digital models.

In some implementations of the method, the reference point is a center of resistance associated with the given tooth.

In some implementations of the method, the reference point is one of a mesial point and a distal point associated with the given tooth.

In some implementations of the method, the method further comprises determining, by the processor, the mesial and distal points associated with the given tooth.

In some implementations of the method, the reference point is a center point of a segmentation contour associated with the given tooth, indicative of a border between the given tooth and a gingiva of the subject.

In some implementations of the method, the method further comprises determining the segmentation contour.

In some implementations of the method, the method further comprises determining the center point of the segmentation contour as being a center point of a bounding box defined around the segmentation contour.

In some implementations of the method, each one of the actual and planned 3D models comprises vertices representative of surfaces of the subject's teeth, and the matching further comprises: applying, by the processor, to the respective representations of the given tooth having been matched by merging the instances of the reference point therein, an alignment algorithm configured to determine correspondences between vertices of the respective representations of the given tooth in the actual and planned 3D digital model.

In some implementations of the method, the alignment algorithm is an iterative closest point (ICP) algorithm.

In some implementations of the method, each one of the actual and planned 3D models comprises vertices representative of surfaces of the subject's teeth, and the matching the respective representations of the given tooth in the actual and planned 3D digital models comprises: during a first individual matching process, merging, by the processor, instances of a reference point associated with the given tooth in the respective representations thereof in the actual and planned 3D digital models; and during a second individual matching process, following the first individual alignment process, applying, by the processor, to the respective representations of the given tooth having been matched by merging the instances of the reference point therein, an alignment algorithm configured to determine correspondences between vertices of the respective representations of the given tooth in the actual and planned 3D digital model.

In some implementations of the method, the respective primitive object is a reference point associated with the given tooth.

In some implementations of the method, the respective primitive object is a polygon.

In some implementations of the method, the polygon is a 2D polygon extending along an occlusal plane associated with the subject's teeth.

In some implementations of the method, the polygon is a 3D polygon.

In some implementations of the method, the 3D polygon is a bounding box defined around the given tooth.

In some implementations of the method, each one of the actual and planned 3D digital model comprises a respective 3D point cloud, the respective 3D point cloud comprising a respective plurality of points representative of surfaces of the subject's teeth in one of the actual and planned positions thereof at the given stage of the current orthodontic treatment plan; the aligning during the first alignment process comprises determining, by the processor, using the outlier detection algorithm, a matching between portions of the respective 3D point clouds representative of the given tooth in the actual and planned positions; and the aligning during the second alignment process comprises determining, by the processor, using the outlier detection algorithm, a matching between the respective 3D point clouds representative of the subject's teeth in the actual and planned positions as a whole.

In some implementations of the method, the aligning during the first alignment process and the second alignment process is executed at least partially concurrently.

In some implementations of the method, the outlier detection algorithm is a random sample consensus (RANSAC) algorithm.

In some implementations of the method, the adjusting the tooth trajectory is executed without changing a number of remaining stages of the current orthodontic treatment plan.

In some implementations of the method, the method further comprises generating, by the processor, along a surface of the actual 3D digital model, a heat map representative of deviation values associated with each one of the subject's teeth; and causing, by the processor, display of the heat map.

Further, in accordance with a second broad aspect of the present technology, there is provided an electronic device for adjusting a current orthodontic treatment plan that has been previously determined for a subject. The current orthodontic treatment plan includes an indication of a tooth trajectory of the given tooth towards a target position thereof. The adjusting comprises determining a deviation value between an actual position and a planned position of a given tooth of the subject at a given stage of the current orthodontic treatment plan. The electronic device comprises a non-transitory computer-readable medium storing instructions; and a processor, which, upon executing the instructions, is configured to: acquire an actual 3D digital model including a representation of each one of the subject's teeth in actual positions thereof at the given stage of the current orthodontic treatment plan; acquire an indication of the current orthodontic treatment plan; generate, based on the current orthodontic treatment plan, a planned 3D digital model including a representation of each one of the subject's teeth in planned positions at the given stage of the current orthodontic treatment plan; align, during a first alignment process, each one of the subject's teeth in the actual 3D digital model and in the planned 3D digital model individually, by: matching (i) a respective representation of the given tooth in the actual 3D digital model with (ii) the respective representation of the given tooth in the planned 3D digital model; align, during a second alignment process following the first alignment process, the subject's teeth in the actual 3D digital model and in the planned 3D digital model, as a whole, by: obtaining, for each one of the subject's teeth, a respective primitive object of a plurality of representative objects; replacing each one of the subject's teeth in the actual and planned 3D digital models with the respective primitive object; and determining, using an outlier detection algorithm, a matching between the plurality of representative objects, as a whole, in the actual and planned 3D digital models; determine the deviation value between the actual and planned positions of the given tooth as a deviation value between positions of the respective primitive object in the actual and planned 3D digital models of the subject's teeth following the second alignment process; and in response to the deviation value being greater than a predetermined deviation threshold, adjust the tooth trajectory of the given tooth to minimize the deviation value associated therewith by an end of the current orthodontic treatment plan.

In some implementations of the electronic device, the processor is further configured to identify the respective representations of the given tooth in the actual and planned 3D digital models based on an ordinal number of the given tooth within a respective arch form of the subject.

In some implementations of the electronic device, the processor is configured to match the respective representations of the given tooth in the actual and planned 3D digital models by: merging instances of a reference point associated with the given tooth in the respective representations thereof in the actual and planned 3D digital models.

In some implementations of the electronic device, each one of the actual and planned 3D models comprises vertices representative of surfaces of the subject's teeth, and the processor is configured to match the respective representations of the given tooth in the actual and planned 3D digital models by: applying to the respective representations of the given tooth having been matched by merging the instances of the reference point therein, an alignment algorithm configured to determine correspondences between vertices of the respective representations of the given tooth in the actual and planned 3D digital model.

In some implementations of the electronic device, the alignment algorithm is an iterative closest point (ICP) algorithm.

In some implementations of the electronic device, each one of the actual and planned 3D models comprises vertices representative of surfaces of the subject's teeth, and the processor is configured to match the respective representations of the given tooth in the actual and planned 3D digital models by: during a first individual matching process, merging instances of a reference point associated with the given tooth in the respective representations thereof in the actual and planned 3D digital models; and during a second individual matching process, following the first individual alignment process, applying to the respective representations of the given tooth having been matched by merging the instances of the reference point therein, an alignment algorithm configured to determine correspondences between vertices of the respective representations of the given tooth in the actual and planned 3D digital model.

In some implementations of the electronic device, the outlier detection algorithm is a random sample consensus (RANSAC) algorithm.

In some implementations of the electronic device, the processor is configured to adjust the tooth trajectory is without changing a number of remaining stages of the current orthodontic treatment plan.

In some implementations of the electronic device, the processor is further configured to: generate, along a surface of the actual 3D digital model, a heat map representative of deviation values associated with each one of the subject's teeth; and cause display of the heat map.

Further, in accordance with a third broad aspect of the present technology, there is provided a method of adjusting a current orthodontic treatment plan having been previously determined for a subject. The current orthodontic treatment plan includes an indication of a tooth trajectory of the given tooth towards a target position thereof. The adjusting comprises determining a deviation value between an actual position and a planned position of a given tooth of the subject at a given stage of the current orthodontic treatment plan. The method is executable by a processor. The method comprises: acquiring, by the processor, an actual 3D digital model including a first plurality of points representative of surfaces of the subject's teeth in actual positions thereof at the given stage of the current orthodontic treatment plan; acquiring, by the processor, an indication of the current orthodontic treatment plan; generating, by the processor, based on the current orthodontic treatment plan, a planned 3D digital model including a second plurality of points representative of surfaces of the subject's teeth in planned positions thereof at the given stage of the current orthodontic treatment plan; determining, by the processor, an alignment between each one of the subject's teeth in the actual 3D digital model and the planned 3D digital model, the determining comprising at least partially concurrent execution of: determining, by the processor, using an outlier detection algorithm, a matching between portions of the first and second plurality of points representative of a surface of the given tooth; and determining, by the processor, using the outlier detection algorithm, a matching between portions of the first and second plurality of points representative of the surfaces of the subject's teeth as a whole; determining, by the processor, the deviation value between the actual and planned positions of the given tooth as a deviation value between instances of a reference point associated with the given tooth in the actual and planned 3D digital models of the subject's teeth following the alignment thereof; and in response to the deviation value being greater than a predetermined deviation threshold, adjusting the tooth trajectory of the given tooth to minimize the deviation value associated therewith by an end of the current orthodontic treatment plan.

In the context of the present specification, unless expressly provided otherwise, the term "orthodontic treatment" is broadly referred to as any type of medical intervention aimed at correcting malocclusions associated with the teeth of the subject or moving the subject's teeth for any reason, including surgical and non-surgical manipulations, such as, but not limited to, using one or more of aligners, brackets, multi-strand wires, strips, retainers, and plates. Further, the orthodontic treatment, as referred to herein, may be determined automatically by a software, based on image data and other inputs associated with the subject, or semi-automatically with input from a practitioner in the field of dentistry (such as an orthodontist, a maxillofacial surgeon, for example).

Further, in the context of the present specification, the term "point cloud 3D representation" of an object (such as a subject's arch form) refers to an image thereof, for example, in a three-dimensional space, comprising a plurality of data points, each of which is defined by a respective set of coordinates (x, y, z), thereby representing a surface of the object. In one example, the point cloud 3D representation of the object may be generated by an imaging device such as a 3D laser scanner, where each laser scan corresponds to a respective data point. Further, the laser scans can be merged, or otherwise registered relative to each other, generating the point cloud 3D representation.

In another example, the point cloud 3D representation of the object may be generated by converting a series of 2D images (or a panoramic video) thereof taken from different angles using, for example, specific software.

In yet another example, the point cloud 3D representation may be generated from a respective mesh 3D representation of the object by omitting data of edges defining mesh elements within the respective 3D mesh model and preserving only data of vertices thereof.

In the context of the present specification, unless expressly provided otherwise, a computer system may refer, but is not limited to, an "electronic device", an "operation system", a "system", a "computer-based system", a "controller unit", a "control device" and/or any combination thereof appropriate to the relevant task at hand.

In the context of the present specification, unless expressly provided otherwise, the expression "computer-readable medium" and "memory" are intended to include media of any nature and kind whatsoever, non-limiting examples of which include RAM, ROM, disks (CD-ROMs, DVDs, floppy disks, hard disk drives, etc.), USB keys, flash memory cards, solid-state-drives, and tape drives.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of embodiments of the present technology will become apparent from the following description, the accompanying drawings and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
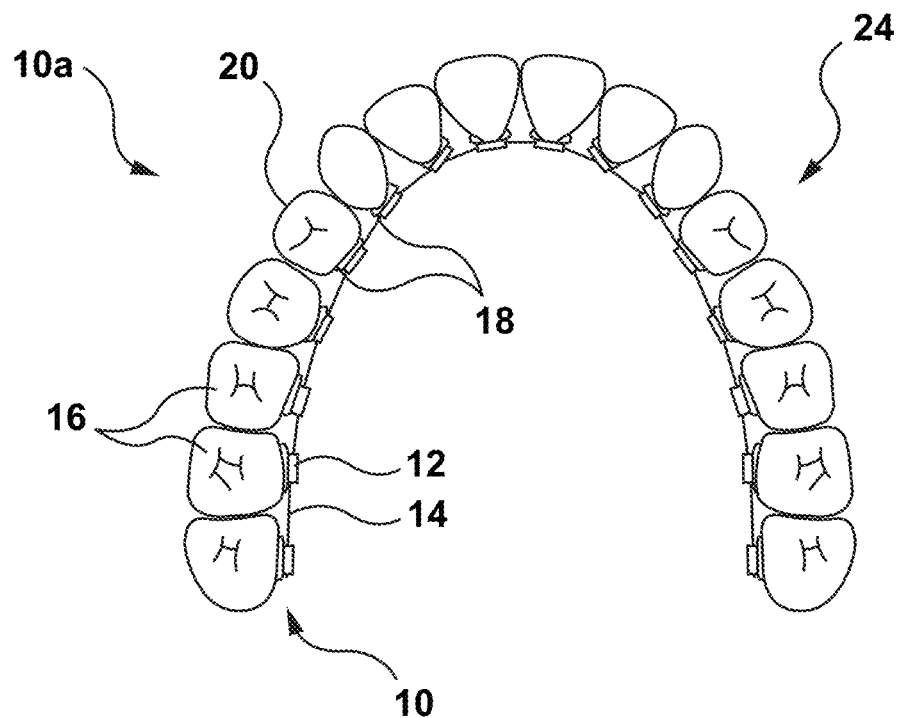
FIG. 1 depicts a schematic diagram of a subject's teeth to which a given orthodontic appliance used for treating orthodontic disorders is attached, in accordance with certain non-limiting embodiments of the present technology.

Certain aspects and embodiments of the present technology are directed to methods and systems for adjusting orthodontic treatment plans during ongoing implementation thereof.

More specifically, the present methods and systems are directed to determining, during the course of a given orthodontic treatment plan, if there is a deviation value between actual and planned positions of at least one tooth of a subject's teeth. In response to determining the deviation value between the planned and actual positions of a given tooth of the subject, the present methods include adjusting the given orthodontic treatment plan such that the deviation value is minimized by an end of the given orthodontic treatment plan.

To determine the deviation value between the actual and planned positions of the given tooth, the present methods are directed to (i) a first alignment process for aligning individual representations (such as 3D meshes, for example) of the subject's teeth in a given arch form in the actual and planned positions thereof; and (ii) a second alignment process, following the first alignment process, for aligning the representations of the entire given arch form.

This sequence of the alignment processes, for achieving a desired accuracy level in determining the deviation value, may enable using an outlier detection algorithm, during the second alignment process, which may be practical in saving computational resources of a processor executing the present methods.

Certain aspects and embodiments of the present technology will now be described below with reference to example orthodontic treatments.

Orthodontic Treatment

Orthodontic treatments are used for treating different conditions relating to teeth misalignment or malocclusion, including but not limited to one or more of: tooth rotation, tooth intrusion/extrusion, tooth translation, and interdental space management. Interdental space management may include one or more of closing embrasures, creating interproximal contacts, opening embrasures, and eliminating interproximal contacts.

An orthodontic appliance 10 used in orthodontic treatments, according to certain non-limiting embodiments of the present technology, include a bracket/archwire system 10a (FIGS. 1 and 2), or an aligner system 10b (FIGS. 3 and 4), amongst others.

It should be expressly understood that, along with the implementations of the orthodontic appliance 10 described herein, it is also contemplated that the orthodontic appliance 10 may be applied in other configurations, such as in a buccal configuration (attached to external surfaces 20 of the upper teeth 16, for example). It is also contemplated that in other non-limiting embodiments of the present technology, the orthodontic appliance 10 may be applied on upper teeth 16 of an upper arch form 24 of the subject in any one of a palatal configuration (attached to inner-sides of teeth of the upper jaw) and a labial configuration (attached to outer-sides of the teeth of the upper jaw) (not shown).

Figure 2:
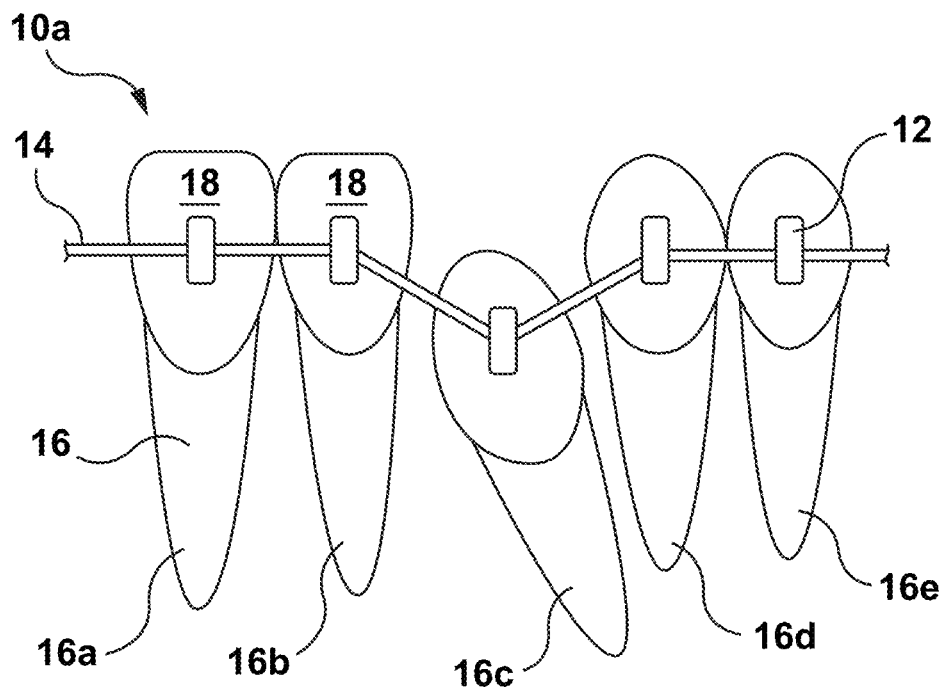
FIG. 2 depicts a schematic diagram of the given orthodontic appliance attached to five teeth of the subject's teeth of FIG. 1, in accordance with certain non-limiting embodiments of the present technology.

In the bracket/archwire system 10a of FIGS. 1 and 2, according to certain non-limiting embodiments of the present technology, there are provided brackets 12 and an archwire 14. The bracket/archwire system 10a is depicted as applied to upper teeth 16 of an upper arch form 24 of a subject (not shown), with the brackets 12 being attached to internal surfaces 18 of the upper teeth 16 in a lingual configuration.

The brackets 12 are provided on respective ones of the upper teeth 16 (shown individually as 16a, 16b, 16c, 16d, 16e in FIG. 2), and the archwire 14 extends between, and is connected to, each of the brackets 12. In the illustrated example, the subject has a malocclusion—that is, a misalignment—of the tooth 16c for which the orthodontic treatment includes an upward movement of the tooth 16c so that the tooth 16c is aligned with the neighboring upper teeth 16a, 16b, 16d, 16e. The archwire 14 is made of a shape memory alloy, such as Nitinol™ and is shaped such that it exerts an upward force to the tooth 16c in use. The archwire 14 can also be made of any other shape memory alloy, or of a material with elastic properties. In certain non-limiting embodiments of the present technology, the bracket/archwire system 10a is designed to impart the orthodontic treatment determined using certain non-limiting embodiments of the present technology of the methods and systems, which will be described below.

Figure 3:
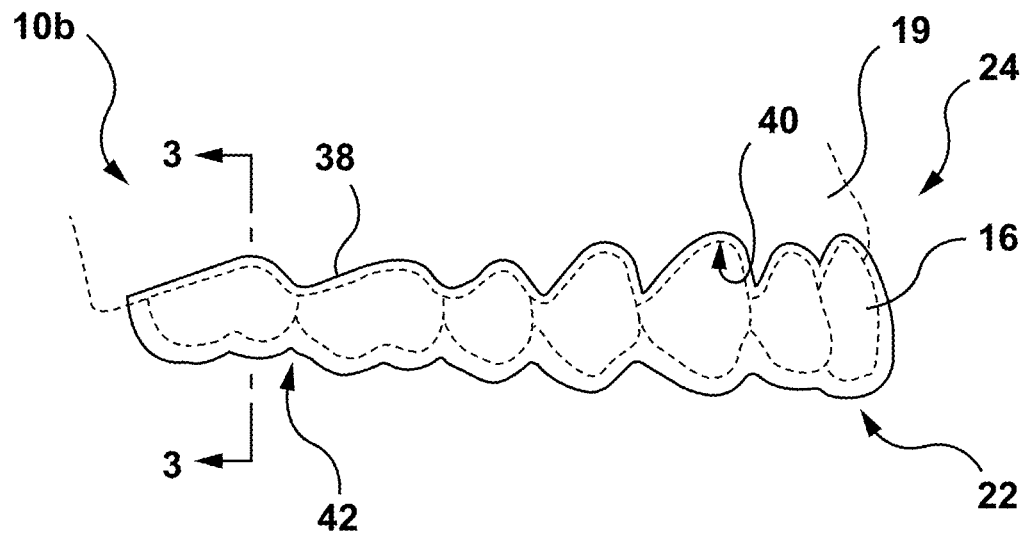
FIGS. 3 and 4 depict side and cross-sectional views, respectively, of another orthodontic appliance which is configured for receiving at least some of the subject's teeth of FIG. 1 for treating the orthodontic disorders, in accordance with certain non-limiting embodiments of the present technology.
Figure 4:
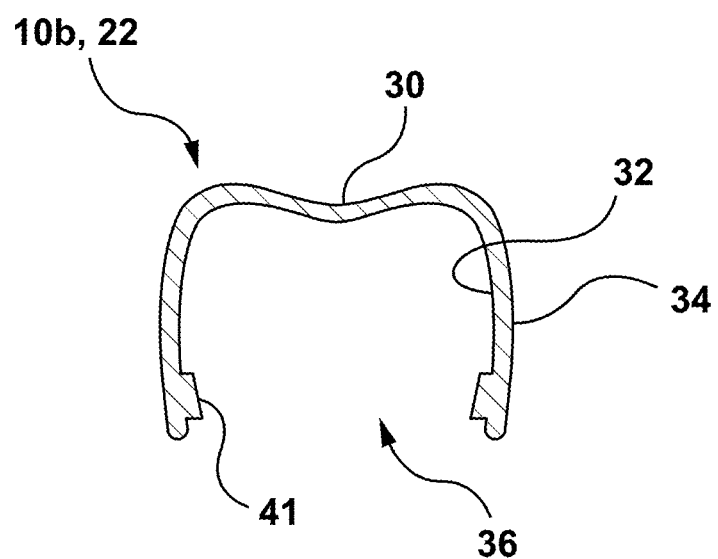

In the aligner system 10b of FIGS. 3 and 4, there is provided an aligner 22 made according to certain aspects and non-limiting embodiments of the present technology, and arranged to impart the orthodontic treatment determined or optimized by methods and systems of the present technology.

As illustrated in FIG. 3, the aligner 22 is for the upper arch form 24 (also referred to as "upper arch" or "upper dental arch") of another subject. However, in other non-limiting embodiments of the present technology (not shown), the aligner 22 is provided for a lower arch form of the subject. In yet other non-limiting embodiments of the present technology, different configurations of the aligner 22 for both the lower arch form and the upper arch form 24 can be provided.

The aligner 22 comprises an aligner body 30 having an inner surface 32 and an outer surface 34. The inner surface 32 defines a channel 36 for receiving at least some upper teeth 16 of the upper arch of the subject. At least one edge 38 of the channel 36 is shaped for intimately following an upper gingiva 19 along a gumline 40 of the subject. In the embodiment of FIGS. 3 and 4, the aligner 22 is arranged to receive all the upper teeth 16 of the upper arch form 24 of the subject. In certain other non-limiting embodiments of the present technology, the aligner 22 is arranged to receive some, not all, of the upper teeth 16.

According to certain non-limiting embodiments of the present technology, a thickness of the aligner body 30, measurable from the inner surface 32 to the outer surface 34 along a direction substantially normal vector to the inner surface 32, is substantially uniform across the aligner body 30.

In other non-limiting embodiments of the present technology, the thickness of the aligner body 30 is variable. For example, in some embodiments, the aligner 22 may further include retentive features for retaining the aligner 22 with respect to the upper teeth 16. Such retentive features can be for example aligner blocks, such as a given block 41, extending outwardly from the inner surface 32 to engage the upper teeth 16 in use. Other retentive features can be aligner recesses defined in the inner surface 32 and sized to engagingly receive blocks affixed to the upper teeth 16 (not shown).

The aligner 22 is made of a polymer, such as a thermoplastic material. In certain non-limiting embodiments of the present technology, the aligner 22 is made of polyvinyl chloride (PVC). In certain other non-limiting embodiments of the present technology, the aligner 22 is made of polyethylene terephthalate glycol (PETG). Other suitable materials can also be used to form the aligner 22. In the case of PETG and PVC, the aligner 22 is substantially transparent. The aligner 22 may be made of other materials having properties that are typically desirable in aligner 22, such as one or more of: low surface roughness, high translucency and mechanical strength adapted for bearing typical orthodontic loads.

It will be appreciated that the present technology can be applied to design and/or make different types, shapes, sizes and configurations of the orthodontic appliance 10, such as, without limitation, multi-strand wires, strips, retainers, and plates. It will also be appreciated that the orthodontic appliance 10 may be used for treating any type of teeth misalignment or malocclusion.

Orthodontic treatments using the orthodontic appliance 10, such as the bracket/archwire system 10a of FIGS. 1 and 2, or the aligner system 10b of FIGS. 3 and 4, comprise sequential treatment steps, in certain non-limiting embodiments of the present technology, in which the orthodontic appliance 10 are applied to the upper teeth 16 at each treatment step to apply forces. The orthodontic appliance 10 and/or applied forces may be the same or different in each treatment step.

Figure 5:
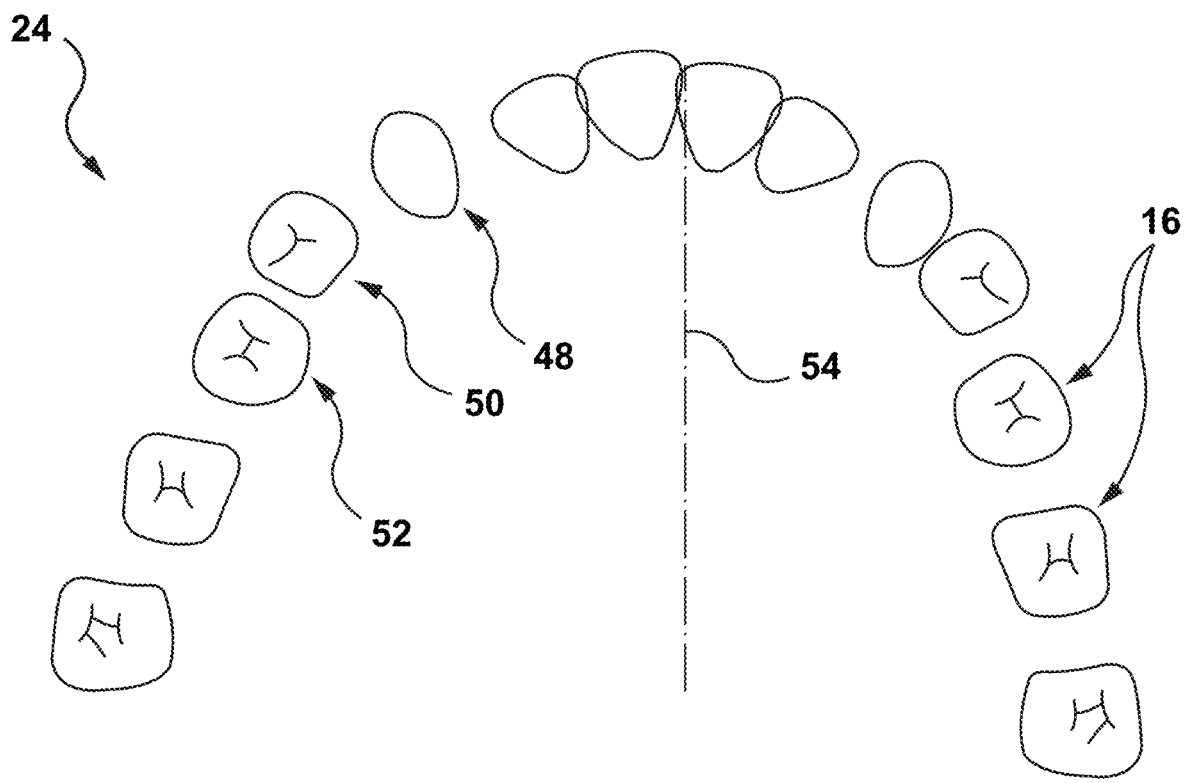
FIGS. 5 and 6 depict a general top view and a magnified top view, respectively, of the subject's teeth in current and desired positions thereof, in accordance with certain non-limiting embodiments of the present technology.
Figure 6:
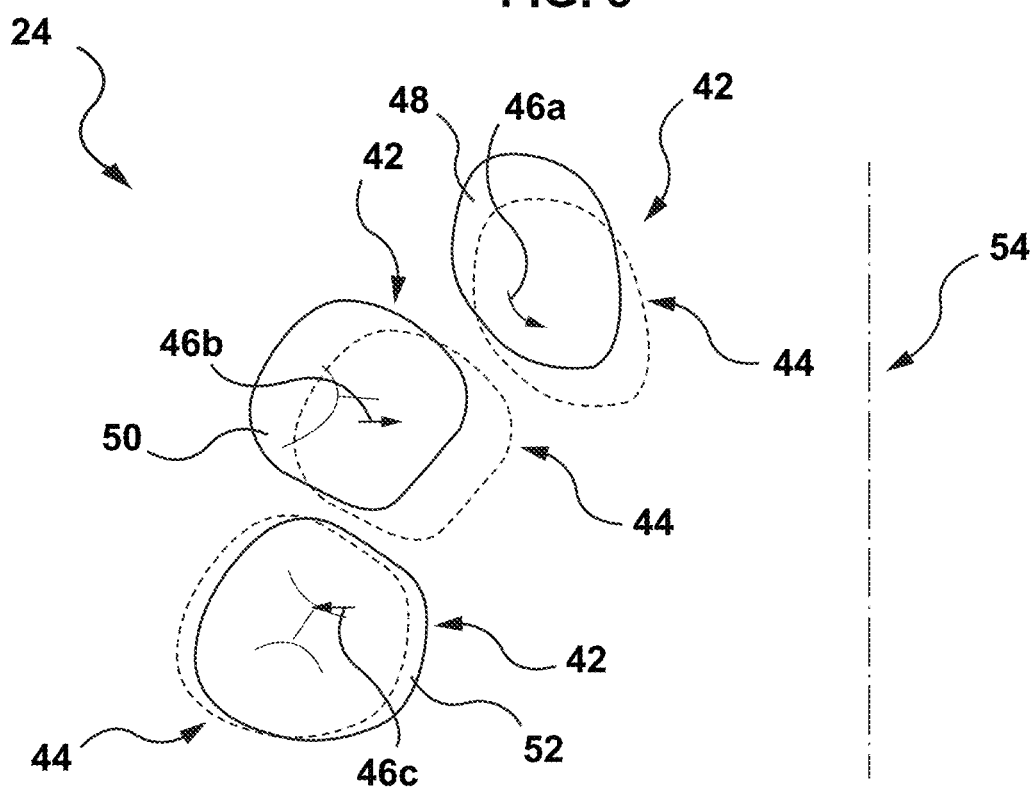

Referring now to FIGS. 5 and 6, generally, in determining the orthodontic treatment, an initial position 42 of the given one of the upper teeth 16 is determined, such as by imaging of the upper teeth 16, using an intraoral scanner, for example, or by taking a physical mold. Desired positions 44 of the upper teeth 16, which can be, for example, associated with alignment of the given one of the upper teeth 16 therewithin, can then be identified. This can be performed manually, semi-automatically, or automatically. In certain non-limiting embodiments of the present technology, the desired position 44 is determined by the orthodontic practitioner. Depending on the initial and desired positions 42, 44 of the upper teeth 16, a respective tooth trajectory of the movement of each of the upper teeth 16 from the initial position 42 to the desired position 44 can be determined. In certain non-limiting embodiments of the present technology, the respective tooth trajectory is one or more of a direct linear path, a plurality of stepped linear paths, and a rotational path.

FIG. 5 depicts a representation of the initial positions 42 of the upper teeth 16 of the subject in the upper arch form 24, and FIG. 6 shows an enlarged view of three of the upper teeth 16 of FIG. 5: an upper right lateral tooth 48, an upper right cuspid tooth 50 and an upper right first bicuspid tooth 52. The initial positions 42 of these three teeth 48, 50, 52 are shown in solid line. The desired positions 44 of each of these three teeth 48, 50, 52 are shown in dotted line. As can be seen, to be positioned in the desired position 44, the upper right lateral tooth 48 will need to be moved laterally and rotationally along a first tooth trajectory 46a, the upper right cuspid tooth 50 will need to be moved linearly towards a middle 54 of the jaw along a second tooth trajectory 46b, and the upper right first bicuspid 52 will need to be moved linearly away from the middle 54 of the jaw along a third tooth trajectory 46c.

As stated above, the orthodontic treatment may comprise a number of treatment steps for moving the given one of the upper teeth 16 from the initial position 42 to the desired position 44. Each treatment step may be defined by a different load provided by different configurations of at least one of the above-mentioned implementations of the orthodontic appliance 10. It may be determined, for example, that the given one of the upper teeth 16 is to be moved 3 mm in three consecutive treatment steps in order to minimize any damage to the upper gingiva 19 and tooth roots.

Certain methods of determination of orthodontic treatment steps in orthodontic treatments are described in a co-owned U.S. Pat. No. 10,993,782-B1 issued on May 4, 2021, and entitled "SYSTEMS AND METHODS FOR DETERMINING A TOOTH TRAJECTORY", the content of which is incorporated herein by reference in its entirety.

More specifically, in these embodiments, the determining a given orthodontic treatment can comprise: (i) acquiring a 3D model of an arch form associated with the subject, the 3D model of the arch form including 3D models of a plurality of subject's teeth including a 3D model of the given tooth, such as at least one of the upper right lateral tooth 48, the upper right cuspid tooth 50, and the upper right first bicuspid tooth 52; (ii) identifying the initial position 42 of the given tooth; (iii) acquiring an indication of the desired position 44 for the given tooth; (iv) acquiring a stress values range for stress applicable to the given tooth for causing the given tooth to move from the initial position 42 to the desired position 44, the stress values range including: a minimum stress value being indicative of a minimum amount of stress for causing the given tooth to move; a maximum stress value being indicative of a minimum amount of stress causing permanent damage to the given tooth; (v) generating, based on the 3D model of the given tooth, a plurality of segments defining the tooth trajectory of the given tooth from the initial position 42 to the desired position 44, a given segment of the plurality of segments being associated with a start position and with an end position, the given segment of the plurality of segments having been generated by executing an optimization algorithm, the executing comprising: (1) identifying the start position associated with the given segment; (2) applying an initial force to the 3D model of the given tooth, the initial force causing a first maximum displacement, in a predetermined interval, of the 3D model of the given tooth from the start position associated with the given segment towards the target position associated with the given tooth; (3) determining, from the first maximum displacement, if there is an occurrence of a collision between the 3D model of the given tooth and a 3D model of at least one adjacent tooth, the collision being caused by applying the initial force; (4) in response to determining that there is the occurrence of the collision, iteratively optimizing, based on the stress values range, the initial force, until: a second maximum displacement of the 3D model of the given tooth is caused, by an optimized initial force, in the predetermined interval, from the start position associated with the given segment towards the desired position 44 associated with the given tooth provided that an extent of the collision between the 3D model of the given tooth and the 3D model of the at least one adjacent tooth is minimized; (vi) determining the optimized initial force as being a valid force to be applied to the given tooth, thereby identifying the end position associated with the given segment.

Also, in some non-limiting embodiments of the present technology, the steps for the orthodontic treatment can be determined in accordance with methods disclosed in a co-owned U.S. Pat. No. 11,259,897-B1 issued on Mar. 1, 2022, and entitled "SYSTEMS AND METHODS FOR DETERMINING AN ORTHODONTIC TREATMENT", the content of which is incorporated herein by reference in its entirety.

Figure 7:
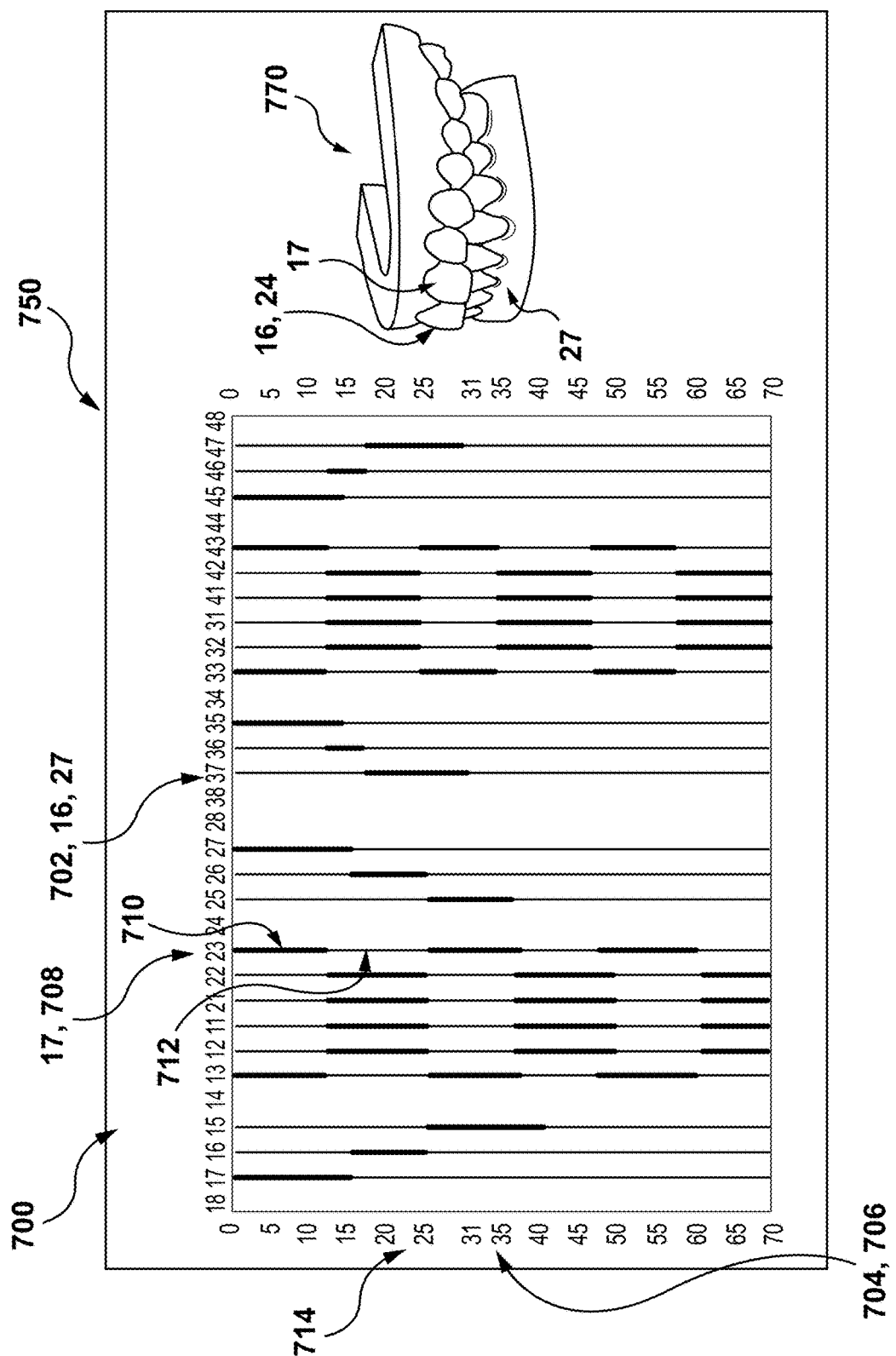
FIG. 7 depicts a planned schedule of a given orthodontic treatment plan for causing the subject's teeth to move towards the desired positions, in accordance with certain non-limiting embodiments of the present technology.

For example, in some non-limiting embodiments of the present technology, a given orthodontic treatment can for the subject's teeth can be represented by a planned schedule 700 schematically depicted in FIG. 7, in accordance with certain non-limiting embodiments of the present technology.

In the depicted embodiments of FIG. 7, the planned schedule 700 includes a horizontal axis 702 representative of respective ordinal numbers of the upper teeth 16 and lower teeth 27; and a vertical axis 1204 representative of a plurality of treatment steps 706 (also refereed to herein as "stages" of the current orthodontic treatment plan) of the given orthodontic treatment (comprising a total of 70 treatment steps in the depicted embodiments). Accordingly, each one of the upper teeth 16 and the lower teeth 27 may thus be associated with the respective tooth trajectory defining path thereof along an associated plurality of segments, during respective ones of the plurality of treatment steps 706. For example, a given tooth 17 of the upper teeth 16 is associated with a respective tooth trajectory 708. According to certain non-limiting embodiments of the present technology, the respective tooth trajectory 708 of the given tooth 17 can include: (i) movement segments, such as a given movement segment 710, along which the given tooth 17 is to move towards the desired position 44; and (ii) resting segments, such as a given resting segment 712, along which the given tooth 17 is to rest, for example, to avoid collisions with neighboring teeth while the neighboring teeth are moving during the corresponding treatment steps.

In other words, the planned schedule 700 can be said to be representative of respective planned positions of the given tooth 17, along the respective tooth trajectory 708, at each one of the plurality of treatment steps 706.

As mentioned above, each of the plurality of treatment steps 706 may be associated with using a respective configuration of the orthodontic appliance 10 configured to apply, during a respective one of the plurality of treatment steps 706, respective forces onto at least one of the upper teeth 16 and the lower teeth 27 causing them to move along respective segments of their associated trajectories. In some non-limiting embodiments of the present technology, each one of the plurality of predetermined treatment steps 706 may be equal and comprise, for example, 14 days. However, in other non-limiting embodiments of the present technology, the plurality of treatment steps 706 may be of various durations each, which may be less than or more than 14 days.

In some non-limiting embodiments of the present technology, the planned schedule 700 may be displayed as a graphical user interface 750 (for example, on a screen 922 of the system 900 schematically depicted in FIG. 9). The planned schedule 700 may thus assist an orthodontic clinician (such as an orthodontist, for example) to monitor the so planned orthodontic treatment and allow modification thereof. In these embodiments, the graphical user interface 750 may include the planned schedule 700 and a 3D digital model 770 representing planned tooth positions of the upper teeth 16 and the lower teeth 27 at each one of the plurality of treatment steps 706 in the course of the orthodontic treatment. In the depicted example of FIG. 7, the 3D digital model 770 is representative of the upper and lower teeth 16, 27 in the desired positions 44, as a result of the planned orthodontic treatment.

Figure 8:
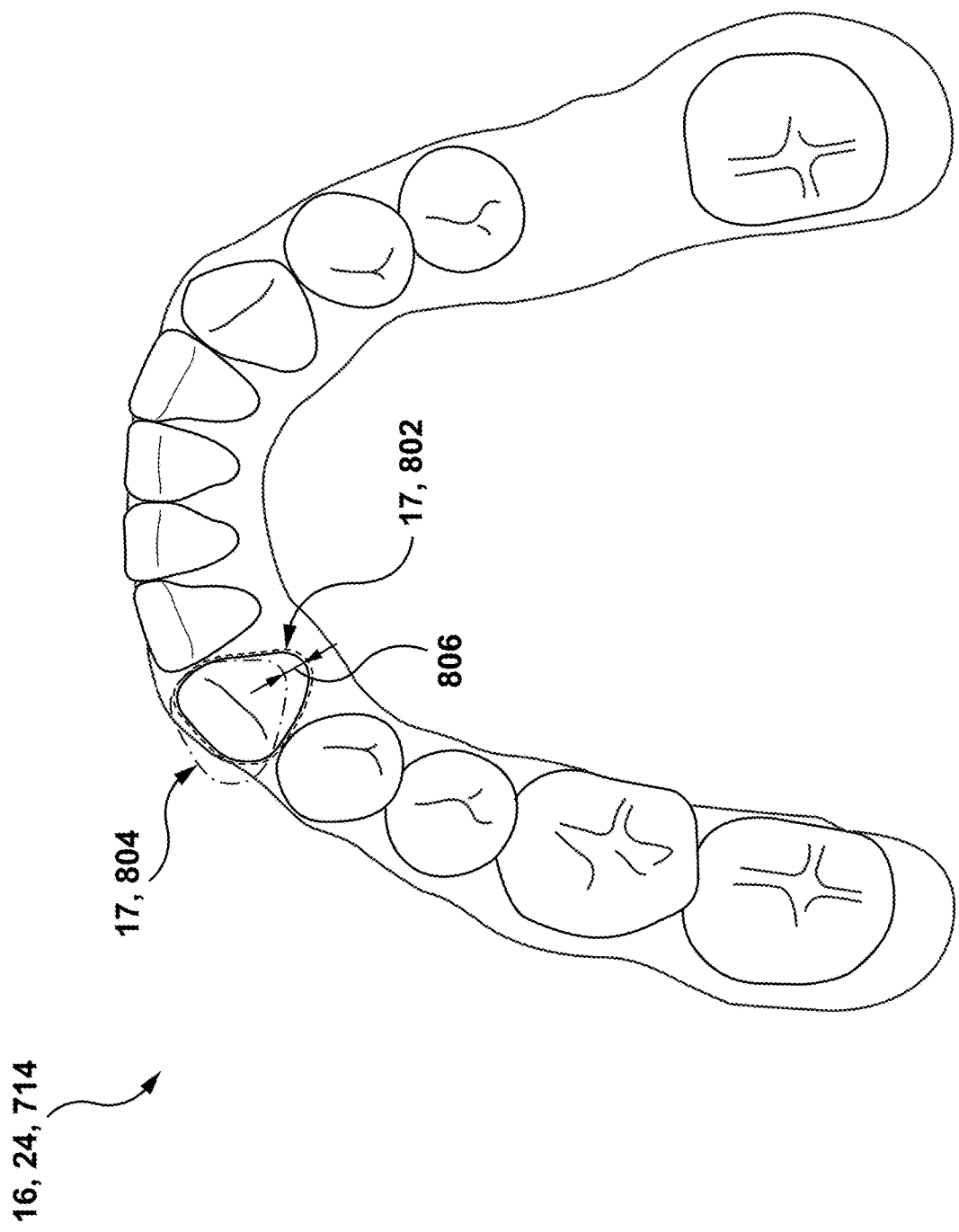
FIG. 8 depicts a bottom elevation view of the subject's teeth illustrating a deviation between an actual position and a planned position of a given tooth of the subject by a given treatment step of the given orthodontic treatment plan, in accordance with certain non-limiting embodiments of the present technology.

However, during the implementation of the given orthodontic treatment plan, at a certain treatment step of the plurality of treatment steps 706, such as a given treatment step 714, an actual position of the given tooth 17 can deviate from its planned position. More specifically, as schematically depicted in FIG. 8, in accordance with certain non-limiting embodiments of the present technology, a respective actual position 802 of the given tooth 17 can be different from a respective planned position 804 of the given tooth 17, with a deviation value 806. In other words, in the example of FIG. 8, the given tooth 17 is falling behind the given orthodontic treatment plan as, by the given treatment step 714, it has not reached the respective planned position 804 associated with the given treatment step 714.

An intuitive approach to annihilating the deviation value 806, would be completely re-determining the given orthodontic treatment plan at the given treatment step 714, that is, generate a new orthodontic treatment plan, hence defining an updated respective tooth trajectory for the given tooth 17 towards the desired position 42. However, the complete re-determination of the orthodontic treatment plan may be considerably time- and resource-intensive. More specifically, for re-determining the given orthodontic treatment plan, there may be required new images associated with the intraoral anatomy of the subject, removal of already mounted orthodontic appliance 10 (such as the bracket/archwire system 10*a*), removal of auxiliary orthodontic appliances (such as attachments or pontics, for example). Also, in terms of computational resources, the re-determination of the given orthodontic treatment may impart a significant strain on a processor.

Thus, the developers of the present technology have appreciated that instead of re-determining the given orthodontic treatment plan, it may be adjusted such that the deviation value 806 is minimized by an end of the given orthodontic treatment plan. More specifically, the present methods and systems are directed to: (i) aligning 3D digital models associated with the upper teeth 16 that are representative of the planned and actual positions of the upper teeth 16 at the given treatment step 714 of the given orthodontic treatment plan; (ii) determining the deviation value 806; and (iii) adjusting the respective tooth trajectory 708 so as to minimize the deviation value 806 by the end of the given orthodontic treatment. The adjusting the respective tooth trajectory 708 may include, for example, increasing the respective forces to be applied to the given tooth 17 during the movement segments of the respective tooth trajectory 708.

How the deviation value can be determined and further minimized, in accordance with certain non-limiting embodiments of the present technology, will be described below with reference to FIGS. 10 to 16.

System

Figure 9A:
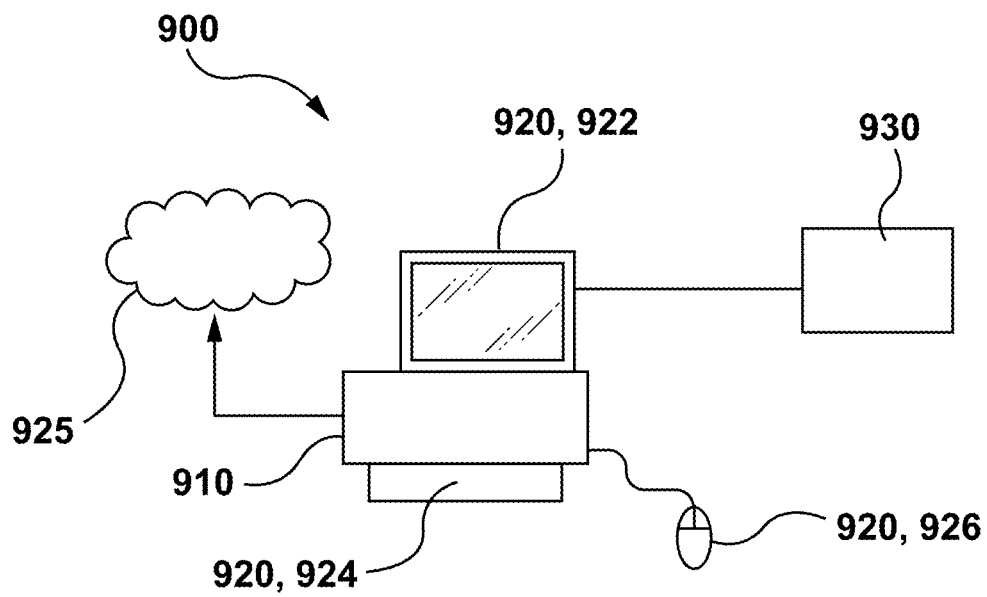
FIG. 9A depicts schematic diagram of a system for adjusting the given orthodontic treatment plan of FIG. 7 to minimize the deviation between the actual and planned positions of the given tooth, in accordance with certain embodiments of the present technology.
Figure 9B:
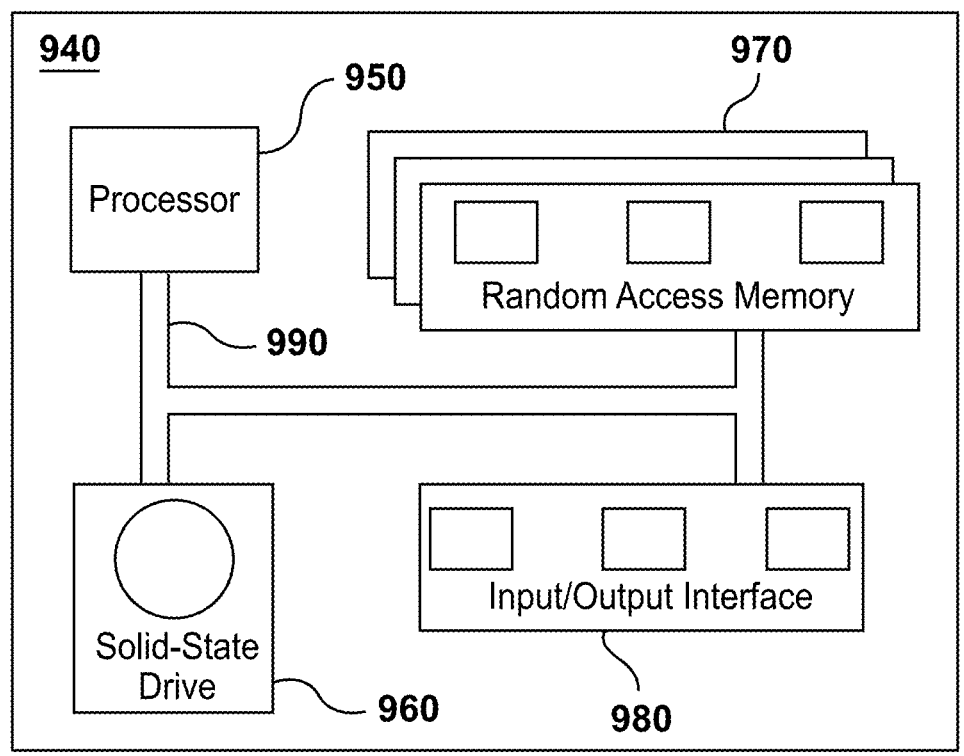
FIG. 9B depicts a schematic diagram of a computing environment of the system of FIG. 9A, in accordance with certain embodiments of the present technology.

With reference to FIGS. 9A and 9B, there is depicted a schematic diagram of a system 900 suitable for adjusting the given orthodontic treatment plan, in accordance with certain non-limiting embodiments of the present technology.

It is to be expressly understood that the system 900 as depicted is merely an illustrative implementation of the present technology. Thus, the description thereof that follows is intended to be only a description of illustrative examples of the present technology. This description is not intended to define the scope or set forth the bounds of the present technology. In some cases, what is believed to be helpful examples of modifications to the system 900 may also be set forth below. This is done merely as an aid to understanding, and, again, not to define the scope or set forth the bounds of the present technology. These modifications are not an exhaustive list, and, as a person skilled in the art would understand, other modifications are likely possible. Further, where this has not been done (i.e., where no examples of modifications have been set forth), it should not be interpreted that no modifications are possible and/or that what is described is the sole manner of implementing that element of the present technology. As a person skilled in the art would understand, this is likely not the case. In addition, it is to be understood that the system 900 may provide in certain instances simple implementations of the present technology, and that where such is the case they have been presented in this manner as an aid to understanding. As persons skilled in the art would further understand, various implementations of the present technology may be of a greater complexity.

In certain non-limiting embodiments of the present technology, the system 900 of FIG. 9A comprises a computer system 910. The computer system 910 may be configured, by pre-stored program instructions, to determine and output, based on image data associated with the subject's teeth, the deviation values between the actual and planned positions of the subject's teeth at the given treatment step 714 of the given orthodontic treatment plan, such as the deviation value 806 associated with the given tooth 17. In some non-limiting embodiments of the present technology, the computer system 910 may further be configured to adjust, based on the deviation value 806, the respective tooth trajectory 708 of the given tooth 17, such that the deviation value 806 by the end of the given orthodontic treatment plan is minimized, as will be described further. It should be noted that in various non-limiting embodiments of the present technology, the computer system 910 may be configured to execute the methods separately and/or independently. Further, the order of these steps may be changed without departing from the scope of the present technology.

To that end, in some non-limiting embodiments of the present technology, the computer system 910 is configured to receive the image data pertaining to the subject or to a given stage of the orthodontic treatment. For example, the computer system 910 may be configured to process the received image data to generate a 3D digital model of the upper arch form 24. According to some non-limiting embodiments of the present technology, the computer system 910 may receive the image data via local input/output interface (such as USB, as an example, not separately depicted). In other non-limiting embodiments of the present technology, the computer system 910 may be configured to receive the image data over a communication network 925, to which the computer system 910 is communicatively coupled.

In some non-limiting embodiments of the present technology, the communication network 925 is the Internet and/or an Intranet. Multiple embodiments of the communication network 925 may be envisioned and will become apparent to the person skilled in the art of the present technology. Further, how a communication link between the computer system 910 and the communication network 925 is implemented will depend, inter alia, on how the computer system 910 is implemented, and may include, but is not limited to, a wire-based communication link and a wireless communication link (such as a Wi-Fi communication network link, a 3G/4G communication network link, and the like).

It should be noted that the computer system 910 can be configured for receiving the image data from a vast range of devices. Some of such devices can be used for capturing and/or processing data pertaining to maxillofacial and/or cranial anatomy of the subject. In certain non-limiting embodiments of the present technology, the image data received from such devices is indicative of properties of anatomical structures of the subject, including: teeth, intraoral mucosa, maxilla, mandible, temporomandibular joint, and nerve pathways, among other structures. In some non-limiting embodiments of the present technology, at least some of the image data is indicative of properties of external portions of the anatomical structures, for example dimensions of a gingival sulcus, and dimensions of an external portion of the given tooth 17 (e.g., a crown portion of the given tooth 17) extending outwardly of the gingival sulcus. In some embodiments, the image data is indicative of properties of internal portions of the anatomical structures, for example volumetric properties of bone surrounding an internal portion of the given tooth 17 (e.g., a root portion of the given tooth 17) extending inwardly of the gingival sulcus. Under certain circumstances, such volumetric properties may be indicative of periodontal anomalies which may be factored into an orthodontic treatment plan. In some non-limiting embodiments of the present technology, the image data includes cephalometric image datasets. In some embodiments, the image data includes datasets generally intended for the practice of endodontics. In some embodiments, the image data includes datasets generally intended for the practice of periodontics.

In alternative non-limiting embodiments of the present technology, the computer system 910 may be configured to receive the image data associated with the subject directly from an imaging device 930 communicatively coupled thereto. Broadly speaking the imaging device 930 may be configured (for example, by a processor 950 depicted in FIG. 9) to capture and/or process the image data of the upper teeth 16 and the periodontium of the subject. In certain non-limiting embodiments of the present technology, the image data may include, for example, one or more of: (1) images of external surfaces of respective crown portions of the upper teeth 16, (2) images of an external surface of the periodontium including those of the upper gingiva 19, the alveolar maxillary bone, and images of superficial blood vessels and nerve pathways associated with the upper teeth 16; and (3) images of an oral region. By doing so, the imaging device 930 may be configured, for example, to capture the image data of the upper arch form 24 including the upper teeth 16 of the subject. It should be noted that although the examples provided herein are directed to receiving and processing the image data of the upper arch form 24 of the subject, it is done solely for the purposes of clarity of explanation of certain non-limiting embodiments of the present technology; therefore, the imaging device 930 may also be configured to capture and/or process image data of the lower arch form (not depicted) of the subject without departing from the scope of the present technology. It should also be noted that the image data may include two-dimensional (2D) data and/or three-dimensional data (3D). Further, in certain non-limiting embodiments of the present technology, the image data includes 2D data, from which 3D data may be derived, and vice versa.

In some non-limiting embodiments of the present technology, the imaging device 930 may comprise an intra-oral scanner enabling to capture direct optical impressions of the upper arch form 24 of the subject.

In a specific non-limiting example, the intraoral scanner can be of one of the types available from MEDIT, CORP. of 23 Goryeodae-ro 22-gil, Seongbuk-gu, Seoul, South Korea. It should be expressly understood that the intraoral scanner can be implemented in any other suitable equipment.

In other non-limiting embodiments of the present technology, the imaging device 930 may comprise a desktop scanner enabling to digitize a mold representing the upper arch form 24. In this regard, the mold may have been obtained via dental impression using a material (such as a polymer, e.g. polyvinyl-siloxane) having been imprinted with the shape of the intraoral anatomy it has been applied to. In the dental impression, a flowable mixture (i.e., dental stone powder mixed with a liquid in certain proportions) may be flowed such that it may, once dried and hardened, form the replica.

In a specific non-limiting example, the desktop scanner can be of one of the types available from DENTAL WINGS, INC. of 2251, ave Letourneux, Montreal (QC), Canada, H1V 2N9. It should be expressly understood that the desktop scanner can be implemented in any other suitable equipment.

In yet other non-limiting embodiments of the present technology, the imaging device 930 can comprise a 3D laser scanner enabling to obtain a respective point cloud 3D representation of the upper arch from 24—such as by scanning the mold thereof and thus registering three-dimensional coordinates of points representative of the surface of the mold.

In a specific non-limiting example, the 3D laser scanner can be of one of the types available from LASER DESIGN of 5900 Golden Hills Drive, Minneapolis, MN 55416. It should be expressly understood that the desktop scanner can be implemented in any other suitable equipment.

Further, it is contemplated that the computer system 910 may be configured for processing of the received image data. The resulting image data of the upper arch form 24 received by the computer system 910 is typically structured as a binary file or an ASCII file, may be discretized in various ways (e.g., point clouds, polygonal meshes, pixels, voxels, implicitly defined geometric shapes), and may be formatted in a vast range of file formats (e.g., STL, OBJ, PLY, DICOM, and various software-specific, proprietary formats). Any image data file format is included within the scope of the present technology. For implementing functions described above, the computer system 910 may further comprise a corresponding computing environment.

With reference to FIG. 9B, there is depicted a schematic diagram of a computing environment 940 suitable for use with some implementations of the present technology. The computing environment 940 comprises various hardware components including one or more single or multi-core processors collectively represented by the processor 950, a solid-state drive 960, a random-access memory 970 and an input/output interface 980. Communication between the various components of the computing environment 940 may be enabled by one or more internal and/or external buses 990 (e.g. a Peripheral Component Interconnect (PCI) bus, universal serial bus (USB), an IEEE 1394 "Firewire" bus, a Small Computer System Interface (SCSI) bus, a Serial-ATA (SATA) bus, an Aeronautical Radio INC (ARINC) bus, etc.), to which the various hardware components are coupled.

The input/output interface 980 allows enabling networking capabilities such as wire or wireless access. As an example, the input/output interface 980 comprises a networking interface such as, but not limited to, a network port, a network socket, a network interface controller and the like. Multiple examples of how the networking interface may be implemented will become apparent to the person skilled in the art of the present technology. For example, but without being limiting, the input/output interface 980 may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 960 stores program instructions suitable for being loaded into the random-access memory 970 and executed by the processor 950, according to certain aspects and embodiments of the present technology. For example, the program instructions may be part of a library or an application.

In some non-limiting embodiments of the present technology, the computing environment 940 is implemented in a generic computer system which is a conventional computer (i.e. an "off the shelf" generic computer system). The generic computer system may be a desktop computer/personal computer, but may also be any other type of electronic device such as, but not limited to, a laptop, a mobile device, a smart phone, a tablet device, or a server.

As persons skilled in the art of the present technology may appreciate, multiple variations as to how the computing environment 940 can be implemented may be envisioned without departing from the scope of the present technology.

Referring back to FIG. 9A, the computer system 910 has at least one interface device 920 for providing an input or an output to a user of the system 900, the at least one interface device 920 being in communication with the input/output interface 980. In the embodiment depicted in FIG. 9A, the interface device is the screen 922. In other non-limiting embodiments of the present technology, the at least one interface device 920 may be a monitor, a speaker, a printer or any other device for providing an output in any form such as an image form, a written form, a printed form, a verbal form, a 3D model form, or the like.

In the depicted embodiments of FIG. 9A, the at least one interface device 920 also comprises a keyboard 924 and a mouse 926 for receiving input from the user of the system 900. Other interface devices 920 for providing an input to the computer system 910 can include, without limitation, a USB port, a microphone, a camera or the like.

The computer system 910 may be connected to other users, such as through their respective clinics, through a server (not depicted). The computer system 910 may also be connected to stock management or client software which could be updated with stock when the orthodontic treatment has been determined and/or schedule appointments or follow-ups with clients, for example.

According to the non-limiting embodiments of the present technology, the processor 950 may be configured to adjust the given orthodontic treatment plan that has been preliminarily determined as mentioned above. How these non-limiting embodiments can be implemented will be described with reference to FIGS. 10 to 16.

Methods

Figure 10:
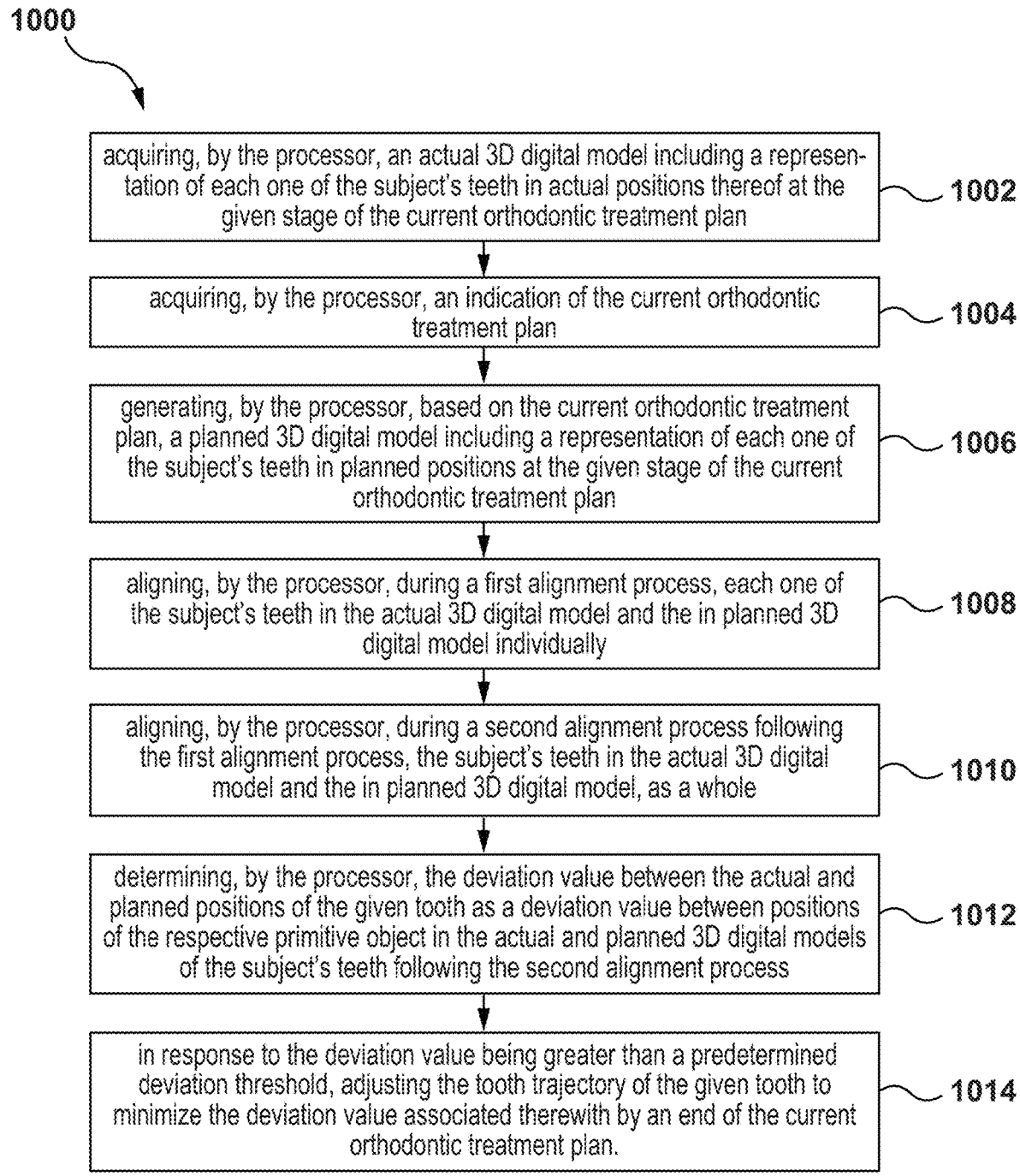
FIG. 10 depicts a flowchart diagram of a method for adjusting, by a processor of FIG. 9B, the given orthodontic treatment plan of FIG. 7 to minimize the deviation between the actual and planned positions of the given tooth.

With reference to FIG. 10, there is depicted a flowchart diagram of a method 1000 for adjusting the given (current) orthodontic treatment plan, in accordance with certain non-limiting embodiments of the present technology. According to certain non-limiting embodiments of the present technology, the method 1000 can be executed by the processor 950 of the computer system 910.

Step 1002: Acquiring, by the Processor, an Actual 3D Digital Model Including a Representation of Each One of the Subject's Teeth in Actual Positions Thereof within the Subject's Gingiva at the Given Stage of the Current Orthodontic Treatment Plan The method 1000 commences at step 1100 with the processor 950 being configured to obtain the image data associated with the subject. More specifically, according to certain non-limiting embodiments of the present technology, at step 1102, the processor 950 can be configured to acquire the image data indicative of the actual positions of the upper teeth 16 of the subject.

Figure 11:
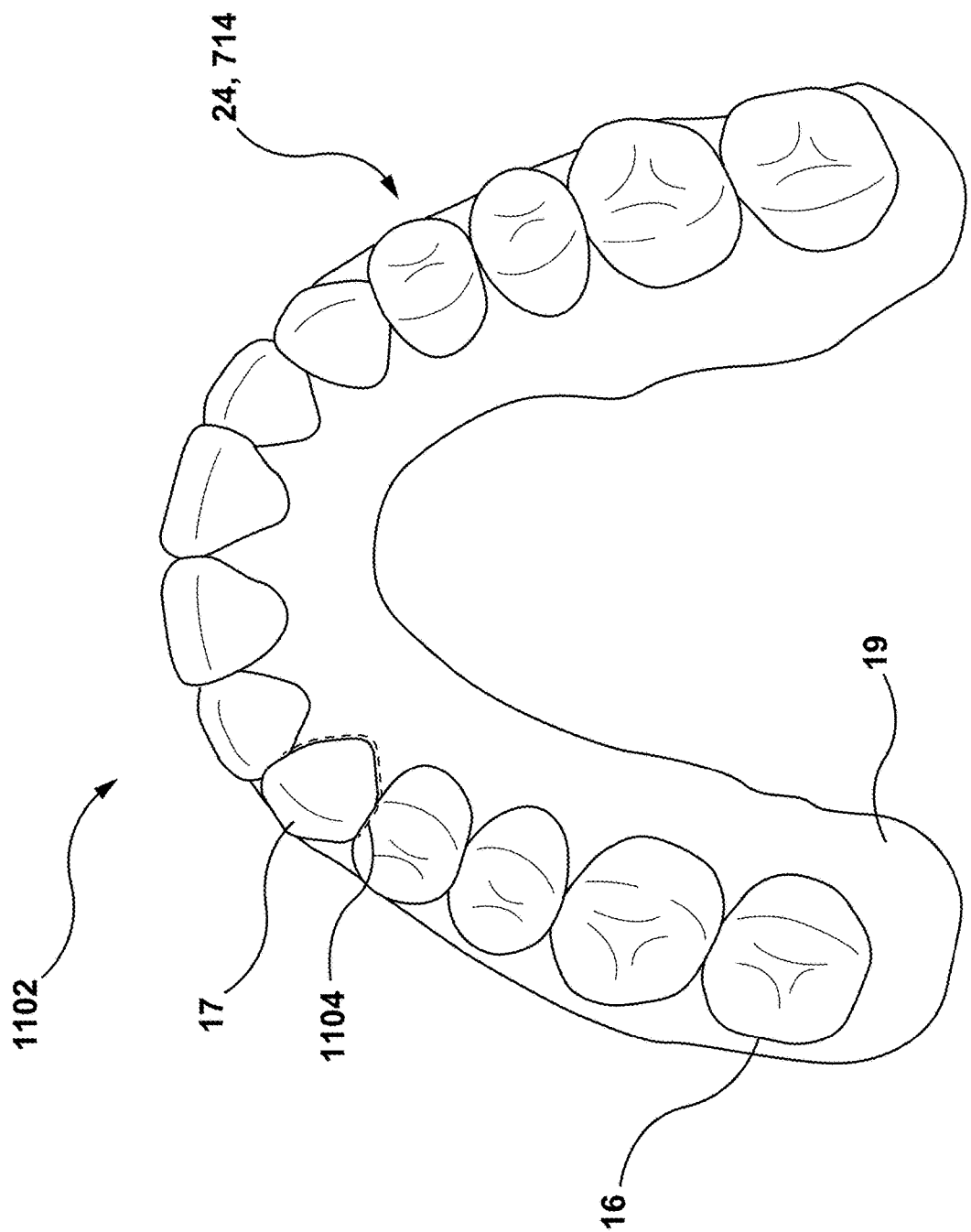
FIG. 11 depicts a perspective view of an actual 3D digital model of the subject's teeth of FIG. 1, representative of actual positions thereof by the given treatment step of the given orthodontic treatment plan, in accordance with certain embodiments of the present technology.

With reference to FIG. 11, there is schematically depicted a perspective view of an actual 3D digital model 1102 representative of the actual positions of the upper teeth 16 at the given treatment step 714 of the current orthodontic treatment, in accordance with certain non-limiting embodiments of the present technology.

In some non-limiting embodiments of the present technology, the actual 3D digital model 1102 is representative of a surface of the upper teeth 16 (also referred to herein as "maxillary teeth") and the upper gingiva 19 in their actual states at the given treatment step 714 of the current orthodontic treatment plan.

In some non-limiting embodiments of the present technology, the processor 950 can be configured to receive, from the imaging device 930 communicatively coupled with the processor 950, the actual 3D digital model 1102 comprising a respective plurality of mesh elements (not depicted) representative of the surface of the upper arch form 24. For example, the imaging device 930 can be configured to generate the plurality of mesh elements including, without limitation, triangular mesh elements, quadrilateral mesh elements, convex polygonal mesh elements, or even concave polygonal mesh elements, as an example, without departing from the scope of the present technology.

As noted hereinabove, in some non-limiting embodiments of the present technology, the actual 3D digital model 1102 may be the respective point cloud 3D representation (not depicted) of the upper arch form 24, including a plurality of points respectively representative of the surface of the upper arch form 24 while the upper teeth 16 are in the respective actual positions thereof within the upper gingiva 19.

In some non-limiting embodiments of the present technology where the imaging device 930 is the 3D laser scanner, the processor 950 may be configured to receive the respective point cloud 3D representation as taken by the imaging device 930. In other non-limiting embodiments of the present technology, where the imaging device 930 is the intraoral scanner providing 3D representations of objects including 3D meshes, to generate the respective point cloud 3D representation of the upper arch form 24, the processor 950 may be configured to pre-process the actual 3D model 1102 to remove image data representative of the mesh edges therefrom leaving only image data representative of the mesh vertices.

It should be noted that it is not limited how the plurality of points are distributed within the actual 3D digital model 1102; and in some non-limiting embodiments of the present technology, the plurality of points may be distributed uniformly within the actual 3D digital model 1102. However, in other non-limiting embodiments of the present technology, the plurality of points may have variable distribution within the actual 3D digital model 1102, such as have higher density in regions representative of the upper teeth 16 and have lower density in regions representative of the upper gingiva 19.

Needless to say, in certain non-limiting embodiments of the present technology, the processor 950 can be configured to generate a similar 3D digital model indicative of a surface of the lower arch form including the lower teeth 27 (also referred to herein as "mandibular teeth") of the subject and a lower gingiva.

Also, as will become apparent from the description provided hereinbelow, in some non-limiting embodiments of the present technology, the processor 950 can be configured to obtain, for each one of the upper teeth 16 in the actual 3D digital model 1102, a respective tooth-gingiva segmentation contour, such a tooth-gingiva segmentation contour 1104 associated with the given tooth 17. According to certain non-limiting embodiments of the present technology, the tooth-gingiva segmentation contour 1104 is a closed contour representative of a boundary between the crown portion of the given tooth 17 and the upper gingiva 19.

In some non-limiting embodiments of the present technology, the processor 950 may be configured to obtain the tooth-gingiva segmentation contour 1104 having been previously generated by third-party software, based on the actual 3D digital model 1102, and data indicative thereof may have been stored in a data format, in which the processor 950 may be configured to receive it, for example, via the input/output interface 980.

In yet other non-limiting embodiments of the present technology, the tooth-gingiva segmentation contour 1104 may be generated manually, for example, by a practicing clinician involved in the determining the orthodontic treatment. For example, the practicing clinician may manually apply the tooth-gingiva segmentation contour 1104 onto the actual 3D digital model 1102, using respective suitable software, and the processor 950 may further be configured to receive the actual 3D digital model 1102, and detect the tooth-gingiva segmentation contour 1104 applied thereon.

In specific non-limiting embodiments of the present technology, the processor 950 may be configured to determine the tooth-gingiva segmentation contour 1104 based on analyzing spatial curvature of the crown portion of the given tooth 17 and that of the upper gingiva 19 around the given tooth 17. More specifically, in this regard, the processor 950 may be configured to apply one of the approaches described in a co-owned U.S. Pat. No. 10,695,147-B1 issued on Jun. 30, 2020, entitled "METHOD AND SYSTEM FOR DENTAL BOUNDARY DETERMINATION", the content of which is hereby incorporated by reference in its entirety.

More specifically, according to certain non-limiting embodiments of the present technology, in order to determine the tooth-gingiva segmentation contour 1104, the processor 950 may be configured to: (i) receive the actual 3D digital model 1102 of the upper arch form 24; (ii) define, around the crown portion of the given tooth 17 in the actual 3D digital model 1102, a tooth-gingiva segmentation contour prototype around it of the tooth-gingiva segmentation contour 1104; (iii) for each vertex of a plurality of vertices of the tooth-gingiva segmentation contour prototype, determine an indication of curvature thereof; (iv) determine, based on the indication of curvature corresponding to the respective vertex, a predicted likelihood parameter for each vertex of the plurality of vertices, wherein the predicted likelihood parameter may indicate a predicted likelihood that a respective vertex corresponds to the tooth-gingiva segmentation contour 1104 between the crown portion and the upper gingiva 19; and (v) use the predicted likelihood parameter of the respective vertices to select the vertices defining the tooth-gingiva segmentation contour 1104.

Further, in some non-limiting embodiments of the present technology, the processor 950 can be configured to segment, in the actual 3D digital model 1102, crown portions of each one of the upper teeth 16 from the upper gingiva 19. How the processor 550 can be configured to segment the crown portions is not limited; and, in some non-limiting embodiments of the present technology, the processor 950 can be configured to apply, to the actual 3D digital model 1102, one or more automatic tooth segmentation approaches described in a co-owned U.S. Pat. No. 10,950,061-B1 issued on Mar. 16, 2021, entitled "SYSTEMS AND METHODS FOR PLANNING AN ORTHODONTIC TREATMENT", content of which is incorporated herein by reference in its entirety.

More specifically, to segment the crown portion of the given tooth 17 within the actual 3D digital model 1102, the processor 950 may be configured to: (i) identify, in the actual 3D digital model 1102, a defined portion forming part of a surface of the given tooth 17, and at least one undefined portion not forming part of the surface of the given tooth 17. According to certain non-limiting embodiments of the present technology, the actual 3D digital model 1102 may comprise the plurality of mesh elements having a plurality of vertices comprising: constrained vertices associated with the defined portion, each constrained vertex having a normal constrained vertex vector; unconstrained vertices initially associated with the undefined portion, each unconstrained vertex having a normal unconstrained vertex vector. Further, according to certain non-limiting embodiments of the present technology, the processor 950 can be configured to: (ii) generate a set of confirmed constrained vertices, including the constrained vertices associated with the defined portion, for identifying and further segmenting, in the actual 3D digital model 1102, the crown portion of the given tooth 17 by: (iii) iteratively, for a given constrained vertex, identifying at least one associated unconstrained vertex which is adjacent to the given constrained vertex in the plurality of mesh elements; (iv) determining an angular difference between the normal constrained vertex vector of the given constrained vertex and the normal unconstrained vertex vector of the at least one associated unconstrained vertex; (v) in response to the angular difference being equal to or below a predetermined threshold value: identifying the at least one associated unconstrained vertex to be a constrained vertex associated with the defined portion for inclusion in the set of confirmed constrained vertices; (vi) in response to the angular difference being above the predetermined threshold value: identifying the at least one associated unconstrained vertex to be an unconstrained vertex associated with the undefined portion for exclusion from the set of confirmed constrained vertices.

Also, in some non-limiting embodiment of the present technology, in addition to the crown portions of the upper teeth 16, the representations thereof in the actual 3D digital model 1102 can include root portions of the upper teeth 16, which can be either generated by the imaging device 930 or reconstructed by the processor 950 based on the representations of the crown portions.

The method 1000 hence advances to step 1004.

Step 1004: Acquiring, by the Processor, an Indication of the Current Orthodontic Treatment Plan At step 1004, according to certain non-limiting embodiments of the present technology, the processor 950 can be configured to receive an indication of the current orthodontic treatment plan. For example, in some non-limiting embodiments of the present technology, the processor 950 can be configured to receive the planned schedule 700 associated with the current orthodontic treatment plan, which was described above with reference to FIG. 7. As mentioned above, the planned schedule 700 includes indications of the planned (or otherwise desired) positions of each one of the upper teeth 16 at each one of the plurality of treatment steps 706.

For example, in some non-limiting embodiments of the present technology, the processor 950 can be configured to determine the current orthodontic treatment plan using approaches described, for example, in one of the co-owned U.S. Pat. Nos. 10,993,782-B1 and 11,259,897-B1 mentioned above.

The method 1000 hence advances to step 1006.

Figure 12:
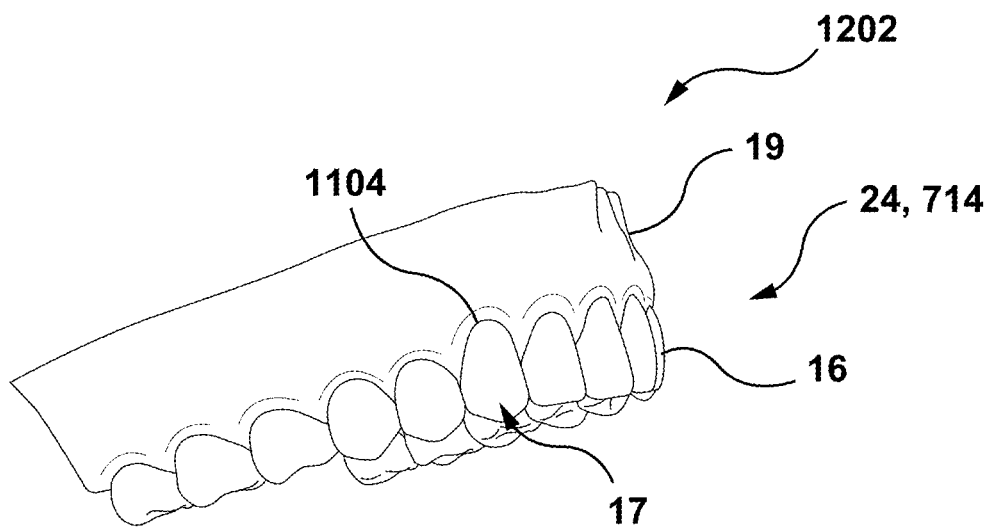
FIG. 12 depicts a perspective view of a planned 3D digital model of the subject's teeth of FIG. 1, representative of planned positions thereof by the given treatment step of the given orthodontic treatment plan, in accordance with certain embodiments of the present technology.

Step 1006: Generating, by the Processor, Based on the Current Orthodontic Treatment Plan, a Planned 3D Digital Model Including a Representation of Each One of the Subject's Teeth in Planned Positions Thereof within a Subject's Gingiva at the Given Stage of the Current Orthodontic Treatment Plan At step 1006, according to certain non-limiting embodiments of the present technology, the processor 950 can be configured to generate, based on the indication of the current orthodontic treatment plan, a planned 3D digital model 1202, which is schematically depicted in FIG. 12 in accordance with certain non-limiting embodiments of the present technology.

According to certain non-limiting embodiments of the present technology, the planned 3D digital model 1202 is representative of the surface of the upper teeth 16 and the upper gingiva 19 of the subject in the planned positions, as prescribed by the current orthodontic treatment plan for the given treatment step 714 of the plurality of treatment steps 706.

According to certain non-limiting embodiments of the present technology, the processor 950 can be configured to generate the planned 3D digital model 1202 based on an initial 3D digital model (not depicted), which is representative of an initial configuration of the upper arch form 24, that is, representative of the initial positions 42 of the upper teeth 16, prior to applying the orthodontic treatment thereto. For example, the processor 950 can be configured to (i) receive the initial 3D digital model from the imaging device 930, which can be executed in a similar manner to receiving the actual 3D digital model 1102; (ii) segment, within the initial 3D digital model, crown portions of each one of the upper teeth 16, for example, as described above with respect to segmenting the crown portions within the actual 3D digital model 1102; and (iii) move each one of the upper teeth 16, in the initial 3D digital model to the respective planned positions of each one of the upper teeth 16 at the given treatment step 714 of the current orthodontic treatment plan, such as the respective planned position 804 of the given tooth 17.

Thus, by modelling the respective planned positions of the upper teeth 16 at the given treatment step 714 of the current orthodontic treatment plan in the initial 3D digital model (not depicted), the processor 950 can be configured to generate the planned 3D digital model 1202 associated with the given treatment step 714.

Needless to mention that, as described above with respect to the generation of the actual 3D digital model 1102, in certain non-limiting embodiments of the present technology, the processor 950 can be configured to generate the planned 3D digital model 1202 comprising one of (i) a respective plurality of mesh elements, such as by the imaging device 930 being the intraoral scanner; and (ii) a respective plurality of points representative of the surface of the upper teeth 16 and the upper gingiva 19 within the upper arch form 24 in the planned positions by the given treatment step 714 of the current orthodontic treatment plan.

Further, the processor 950 can be configured to obtain the respective tooth-gingiva segmentation contours for each one the upper teeth in the planned 3D digital model 1202 in a similar manner as described above at step 1002 with respect to the actual 3D digital model 1102.

Thus, having acquired the actual and planned 3D digital models 1102, 1202 of the upper teeth 16 of the subject for the given treatment step 714 of the current orthodontic treatment, the processor 950 can further be configured to determine the deviation value 806 between the respective actual and planned positions 802, 804 of the given tooth 17 for further use in adjusting the current orthodontic treatment. To do so, first, the processor 950 can be configured to identify representations of each one of the upper teeth 16 in each one of the actual and planned 3D digital models 1102, 1202. In some non-limiting embodiments of the present technology, the processor 950 can be configured to identify corresponding representations of the upper teeth 16 in each one of the actual and planned 3D digital models 1102, 1202, by ordinal numbers of the upper teeth 16 within the upper arch form 24, for example, according to the Universal Numbering System (International Standard Organization 3950). For example, according to this system, as marked in each one the actual and planned 3D digital models 1102, 1202 in FIGS. 11 and 12, respectively, the given tooth 17 is sixth within the upper arch form 24.

Further, the processor 950 can be configured to align the representations of each one of the upper teeth 16 in the actual and planned 3D digital models 1102, 1202, which, according to certain non-limiting embodiments of the present technology, can include: (1) a first alignment process, where the processor 950 can be configured to align the representations of each of the upper teeth 16 in the actual and planned 3D digital models 1102, 1202 relative to each other individually; and (2) a second alignment process, where the processor 950 can be configured to align the representations of the upper teeth 16 as a whole, that is, the entire representations of the upper arch form 24 in the actual and planned 3D digital models 1102, 1202.

The first and second alignment processes will be described below at the respective steps of the method 1000.

The method 1000 hence advances to step 1008.

Figure 13:
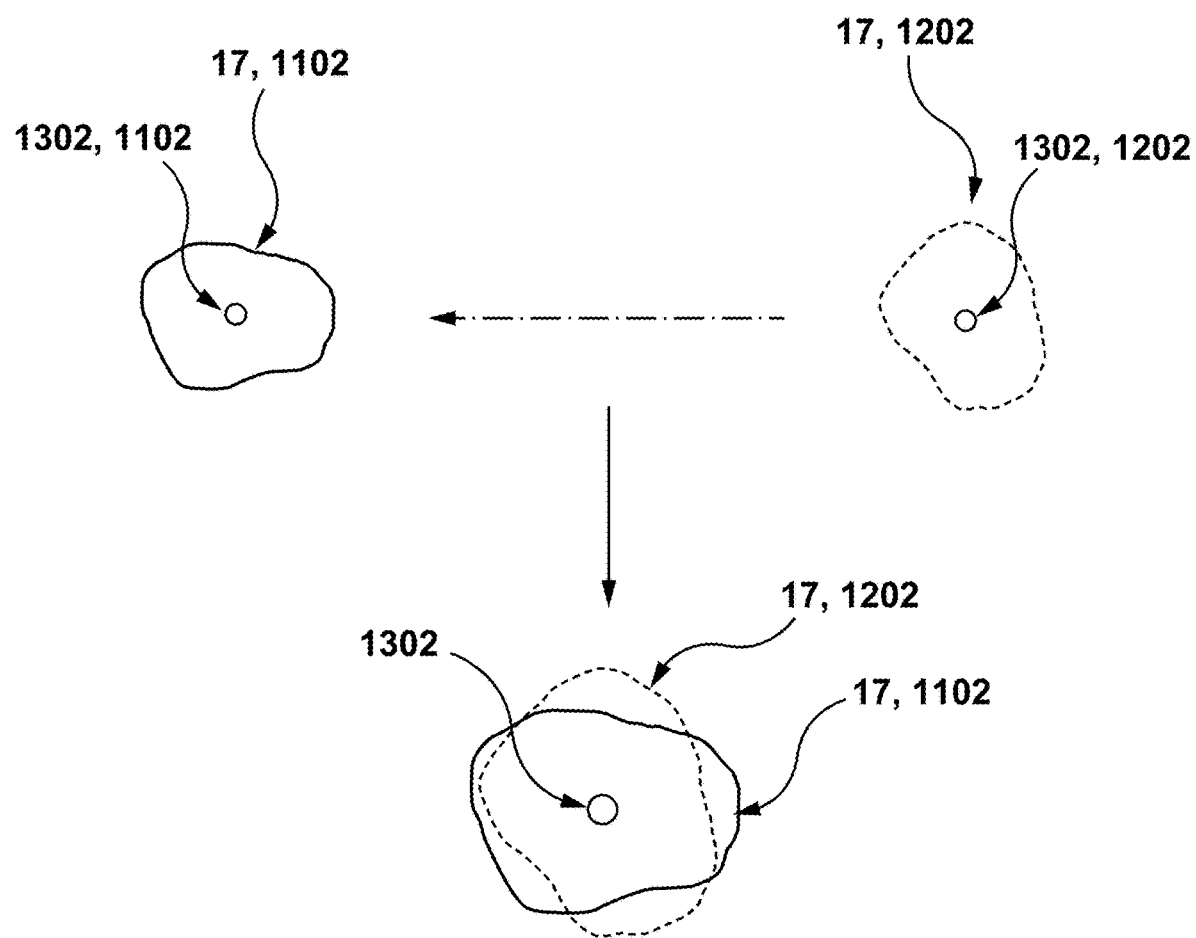
FIG. 13 depicts a schematic diagram of an individual alignment, by the processor of FIG. 9B, between representations of the subject's teeth in the actual and planned 3D digital models of FIGS. 11 and 12, respectively, in accordance with certain non-limiting embodiments of the present technology.

Step 1008: Aligning, by the Processor, During a First Alignment Process, Each One of the Subject's Teeth in the Actual 3D Digital Model and in the Planned 3D Digital Model Individually At step 1008, the processor 950 can be configured to execute the first alignment process between the representations of the given tooth 17 in the actual and planned 3D digital models 1102, 1202, a schematic diagram of which, illustrating top views of the given tooth 17 therein, is depicted in FIG. 13, in accordance with certain non-limiting embodiments of the present technology.

More specifically, according to certain non-limiting embodiments of the present technology, to execute the first alignment process, the processor 950 can be configured to match the representation of the given tooth 17 in the actual 3D digital model 1102 with the representation of the given tooth 17 in the planned 3D digital model 1202. To do so, according to certain non-limiting embodiments of the present technology, the processor 950 can be configured to: (i) identify, within the representations of the given tooth 17 in each one of the actual and planned 3D digital models 1102, 1202, a reference point 1302; and (ii) merge instances of the reference point 1302 in the actual and planned 3D digital models 1102, 1202.

In some non-limiting embodiments of the present technology, the processor 950 can be configured to determine the reference point 1302 as being a center of resistance (CR) point associated with the given tooth 17. In the context of the present specification, the term "CR point" of a given body, such as the given tooth 17, denotes broadly a point, at which imposing a given mechanical force results in a translational movement (or otherwise, a bodily movement) of the given tooth 17 in a direction of a line of action of the given mechanical force.

It is not limited how the processor 950 can be configured to determine the CR point for the given tooth 17; however, in some non-limiting embodiments of the present technology, the processor 950 can be configured to apply one or more approaches described in co-owned U.S. Pat. No. 10,856,954-B1 issued on Dec. 8, 2020 and entitled "SYSTEMS AND METHODS FOR DETERMINING TOOTH CENTER OF RESISTANCE", the content of which is incorporated herein by reference in its entirety.

More specifically, in order to determine the CR point of the given tooth 17, the processor 950 can be configured to: (i) receive image data associated with the crown portion of the given tooth 17, such as one of the actual and planned 3D digital models of the upper teeth 16; (ii) identify a mesiodistal center of the crown portion of the given tooth 17, including obtaining a mesial point on a mesial side of the crown portion, and a distal point on a distal side of the crown portion, generating a mesiodistal line joining the mesial point and the distal point, and identifying the mesiodistal center as a midpoint on the mesiodistal line; (iii) determine, in the crown portion of the given tooth in one of the actual and planned 3D digital models 1102, 1202, a reference plane, which is perpendicular to the mesiodistal line and extending through the mesiodistal center; (iv) determine an intersection curve based on an intersection of the reference plane and a representation of the given tooth 17, the intersection curve following a shape of the surface of the crown portion of the given tooth 17 at the reference plane in the one of the actual and planed 3D digital models 1102, 1202; (v) determine a tooth axis (such as a tooth axis 1404 depicted in FIG. 14B) of the crown portion of the given tooth 17 based on the intersection curve; (vi) determine a crown height of the crown portion based on the tooth axis; and (vii) determine the CR point of the given tooth 17 tooth based on the determined crown height and the determined tooth axis.

Embodiments where the CR point is obtained from the practicing clinician are also envisioned without departing from the scope of the present technology.

However, in other non-limiting embodiments of the present technology, the processor 950 can be configured to determine the reference point 1302 as one of the mesial and distal points (not depicted) associated with the given tooth 17. In the context of the present specification the mesial and distal points associated with the given tooth 17 are indicative of projections of contact regions thereof with neighboring teeth to an occlusal plane of the given tooth 17. For example, in some non-limiting embodiments of the present technology, the mesial and distal points can be determined by the orthodontic clinician. However, in other non-limiting embodiments of the present technology, the processor 950 can be configured to determine the mesial and distal points associated with the given tooth 17 using one of the approaches described in a co-owned U.S. patent application Ser. No. 18/116,485, filed on Mar. 2, 2023, and entitled "SYSTEM AND A METHOD FOR DETERMINING A TOOTH T-MARKING", the content of which is incorporated herein by reference in its entirety.

More specifically, in these embodiments, the processor 950 can be configured to: (i) obtain a reference plane which extends along an occlusal surface of the given tooth 17; (ii) generate groupings of the mesh elements representative of the given tooth 17 in a given one of the actual and planed 3D digital models 1102, 1202, each grouping comprising a sub-group of the mesh elements connecting a respective sub-group of vertices in a tree-like configuration, the groupings being based on one or more apices of the surface of the given tooth 17; (iii) identify normal vectors at vertices defining each grouping, and projecting the normal vectors onto the reference plane; determining a labiolingual line as a line, extending in the reference plane, which is a line of best fit of ends of the projected unitized normal vectors with starts in plane origin; (iv) determine a mesiodistal line as a line extending in the reference plane through the reference plane origin and perpendicular to the labiolingual line; and (v) determine the mesial and distal points associated with the given tooth 17 as points of intersection between the mesiodistal line and the occlusal surface of the given tooth 17 in the given one of the actual and planned 3D digital models 1102, 1202.

In yet other non-limiting embodiments of the present technology, the processor 950 can be configured to determine the reference point 1302 associated with the given tooth 17 as a geometric center of a bounding box (not depicted) defined around the representation of the crown portion of the given tooth 17 in the given one of the actual and planed 3D digital models 1102, 1202. Broadly, the term "bounding box" refers to a three-dimensional box (or a parallelepiped) of a smallest possible measure (such as an area or a volume thereof) allowing for entirely enclosing a given point set, such as vertices representative of the crown portion of the given tooth 17 in the given one of the actual and planned 3D digital models 1102, 1202.

In yet other non-limiting embodiments of the present technology, the processor 950 can be configured to determine the reference point 1302 for the given tooth 17 as a geometric center of an area enclosed within the tooth-gingiva segmentation contour 1104 associated with the given tooth 17. For example, the processor 950 can be configured to determine the geometric center of the area enclosed within the tooth-gingiva segmentation contour 1104 as a geometric center of a bounding box defined around the tooth-gingiva segmentation contour 1104.

It should be noted that, in some non-limiting embodiments of the present technology, for executing the first alignment process for the given tooth 17, instead of using a single reference point, that is, the reference point 1302, the processor 950 can be configured to use a plurality of reference points, including, for example, two, three, ten, or twenty reference points. Similarly, in these embodiments, the processor 950 can be configured to: (i) identify each one of the plurality of reference points along or within the surface of the given tooth 17 in each one of the actual and planned 3D digital models 1102, 1202; and (ii) merge respective instances of each one of the plurality of reference points as described above with respect to the reference point 1302.

By way of example only, the processor 950 can be configured to identify, in each one of the actual and planned 3D digital models 1102, 1202: (i) a first one of the plurality of reference points within the surface of the given tooth 17, such as a center of the bounding box defined therearound; and (ii) and a second one of the plurality of reference points along the surface of the given tooth 17, such as one of the mesial and distal points on the occlusal surface of the crown portion of the given tooth 17.

Additionally, in some non-limiting embodiments of the present technology, for executing the first alignment process, for further alignment of the representations of the given tooth 17 in the actual and planned 3D digital models 1102, 1202, the processor 950 can be configured to: (i) identify, in each one of the actual and planned 3D digital models 1102, 1202, vertices defining the surface of the given tooth 17; and (ii) identify correspondences between instances of the vertices defining the surface of the given tooth 17 in each one of the actual and planned 3D digital models 1102, 1202; and (iii) by iteratively minimizing respective distances between the instances of the vertices in each one of the actual and planned 3D digital models 1102, 1202, match therein the representations of the given tooth 17. According to certain non-limiting embodiments of the present technology, to identify the correspondences between the instances of the vertices defining the surface of the given tooth 17 and minimize the respective distances therebetween, the processor 950 can be configured to apply an alignment algorithm, including, for example, an Iterative Closest Point (ICP) algorithm.

The method 1000 hence advances to step 1010.

Step 1010: Aligning, by the Processor, During a Second Alignment Process Following the First Alignment Process, the Subject's Teeth in the Actual 3D Digital Model and in the Planned 3D Digital Model, as a Whole At step 1010, after aligning the representations of the given tooth 17 relative to each other during the first alignment process, according to certain non-limiting embodiments of the present technology, the processor 950 can be configured to execute the second alignment process, that is, aligning the representations of the upper teeth 16 as a whole in each one of the actual and planned 3D digital models 1102, 1202.

According to certain non-limiting embodiments of the present technology, prior to executing the second alignment process, the processor 950 can be configured to replace the representations of each one of the upper teeth 16, aligned individually relative to each other as described above at step 1008, in each one of the actual and planned 3D digital models 1102, 1202, with a respective primitive object.

According to certain non-limiting embodiments of the present technology, various implementations of the respective primitive object are envisioned. For example, in some non-limiting embodiments of the present technology, the respective primitive object can be a 2D object. The 2D object can include, without limitation: a circle, a 2D polygon, such as a square, a rectangle, a triangle, and the like. In these embodiments, the processor 950 can be configured to replace the representation of the given tooth 17 in each one of the actual and planned 3D digital models 1102, 1202 with the respective primitive object such that the respective primitive object is perpendicular to the tooth axis 1404 associated with the given tooth 17 depicted in FIG. 14B, determined as described above with respect to the CR point with reference to FIG. 13. Also, in these embodiments, a center of the respective primitive object can be positioned at the tooth axis 1404.

However, in other non-limiting embodiments of the present technology, the respective primitive object can be a 3D object, including, without limitation: a sphere, a 3D polygon (such as a prism, a cube, a parallelepiped, and the like), and others. Also, in yet other non-limiting embodiments of the present technology, the respective primitive object associated with the given tooth 17 in each one of the actual and planned 3D digital models 1102, 1202 can be the reference point 1302 determined as described above with reference to FIG. 13.

Figure 14A:
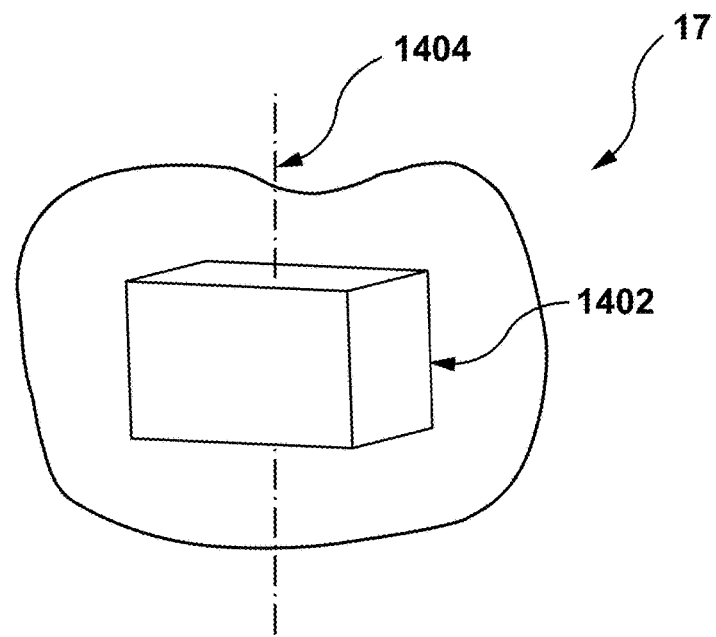
FIG. 14A depicts a schematic diagram of an example primitive object for replacing, by the processor of FIG. 9B, the given tooth in each one of the actual and planned 3D digital models of FIGS. 11 and 12, respectively, in accordance with certain non-limiting embodiments of the present technology.

With reference to FIG. 14A, there is depicted a schematic diagram of a respective 3D polygon 1402 for replacing the representations of the given tooth 17 in each of the actual and planned 3D digital models 1102, 1202, in accordance with certain non-limiting embodiments of the present technology.

As it can be appreciated, in certain non-limiting embodiments of the present technology, the processor 950 can be configured to replace the representation of the given tooth 17 with the respective 3D polygon 1402 such that an axis of symmetry of the respective 3D polygon 1402 is colinear with the tooth axis 1404 associated with the given tooth 17.

In some non-limiting embodiments of the present technology, the respective 3D polygon 1402 can be enclosed within the surface of the given tooth 17 in each one of the actual and planned 3D digital models 1102, 1202. In these embodiments, dimensions of each 3D polygon associated with a respective one of the upper teeth 16 can be constant (that is, independent from the respective one of the upper teeth 16) and selected such that each 3D polygon, such as the respective 3D polygon 1402, can be enclosed within the surface of a smallest tooth of the upper teeth 16. In another example, the dimensions of the respective 3D polygon 1402 can be reflective of dimensions of the given tooth 17, for example, proportional thereto.

However, in other non-limiting embodiments of the present technology, the respective 3D polygon 1402 can be generated around the surface of the given tooth 17 in each one of the actual and planned 3D digital models 1102, 1202. For example, in these embodiments, the processor 950 can be configured to generate the respective 3D polygon 1402 as a bounding box around the surface of the crown portion of the given tooth 17 in each one of the actual and planned 3D digital models 1102, 1202.

Figure 14B:
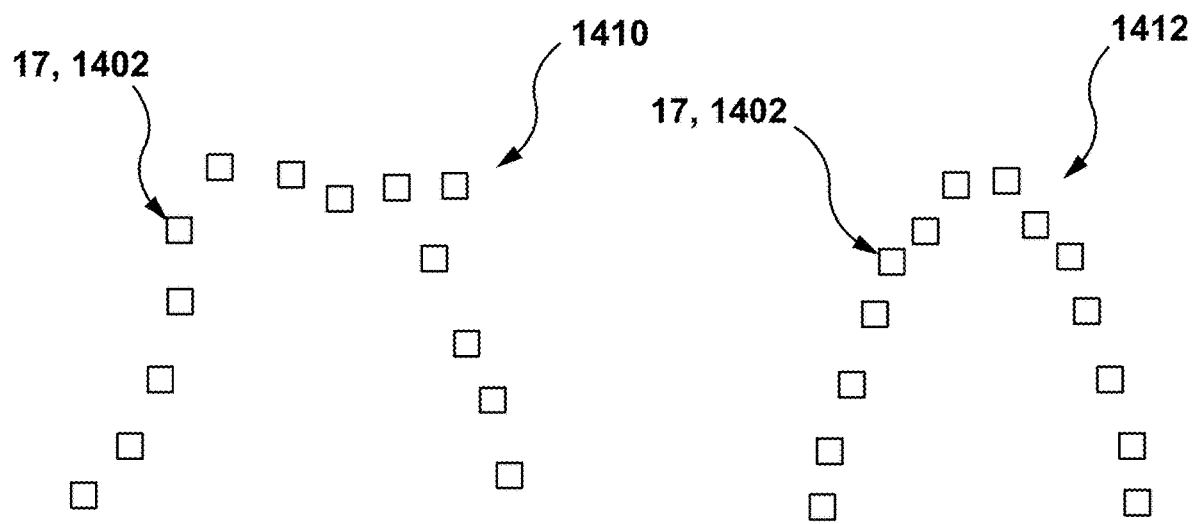
FIG. 14B depicts a bottom elevation view of the actual and planned 3D digital models of FIGS. 11 and 12, where the representations of the subject's teeth have been replaced by respective primitive objects, for aligning the representations of the subject's teeth in the actual and planned positions thereof as a whole, in accordance with certain non-limiting embodiments of the present technology.

Further, after replacing the representations of each one of the upper teeth 16 in the actual and planned 3D digital models 1102, 1202 with the respective primitive objects, the processor 950 can be configured to execute the second alignment process. With reference to FIG. 14B, there is depicted a schematic diagram of a top view of an actual distribution of 3D polygons 1410 and a planned distribution of the 3D polygons 1412, having been generated by replacing the representations of the upper teeth 16 in each one of the actual and planned 3D digital models 1102, 1202, respectively, by 3D polygons, in accordance with certain non-limiting embodiments of the present technology.

To execute the second alignment process, in some non-limiting embodiments of the present technology, the processor 950 can be configured to execute an outlier detection algorithm. Broadly speaking, the outlier detection algorithm is configured to determine an alignment between a first data set, such as the actual distribution of the 3D polygons 1410, and a second data set, such as the planned distribution of 3D polygons 1412, by determining a best fit therebetween. In various non-limiting embodiments of the present technology, the outlier detection algorithm can be implemented, without limitation, based on one of: (i) statistical approaches (such as a Z-score approach, a Tukey's range approach, and a Grubbs's approach, for example), (ii) machine-learning models (MLM, such as a one-class support vector MLM, a replicator neural network, a Hidden Markov MLM and the like), and (iii) clustering algorithms (such as a k-nearest neighbors algorithm, a local outlier factor algorithm, and the like).

In some non-limiting embodiments of the present technology, the outlier detection algorithm can be based on a repeated sub-sampling method, and comprise, for example, a RANdom SAmple Consensus (RANSAC) algorithm. In these embodiments, to determine an alignment between the actual and planned distribution of 3D polygons 1410, 1412, as a whole, the outlier detection algorithm can be configured to iteratively execute the following steps:

selecting a random subset of the planned distribution of the 3D polygons 1412;

fitting the the actual distribution of 3D polygons 1410 to the selected subset of the planned distribution of the 3D polygons 1412; and determining a number of outliers between the actual distribution of the 3D polygons 1410 and the selected subset from the planned distribution of the 3D polygons 1412.

Figure 15:
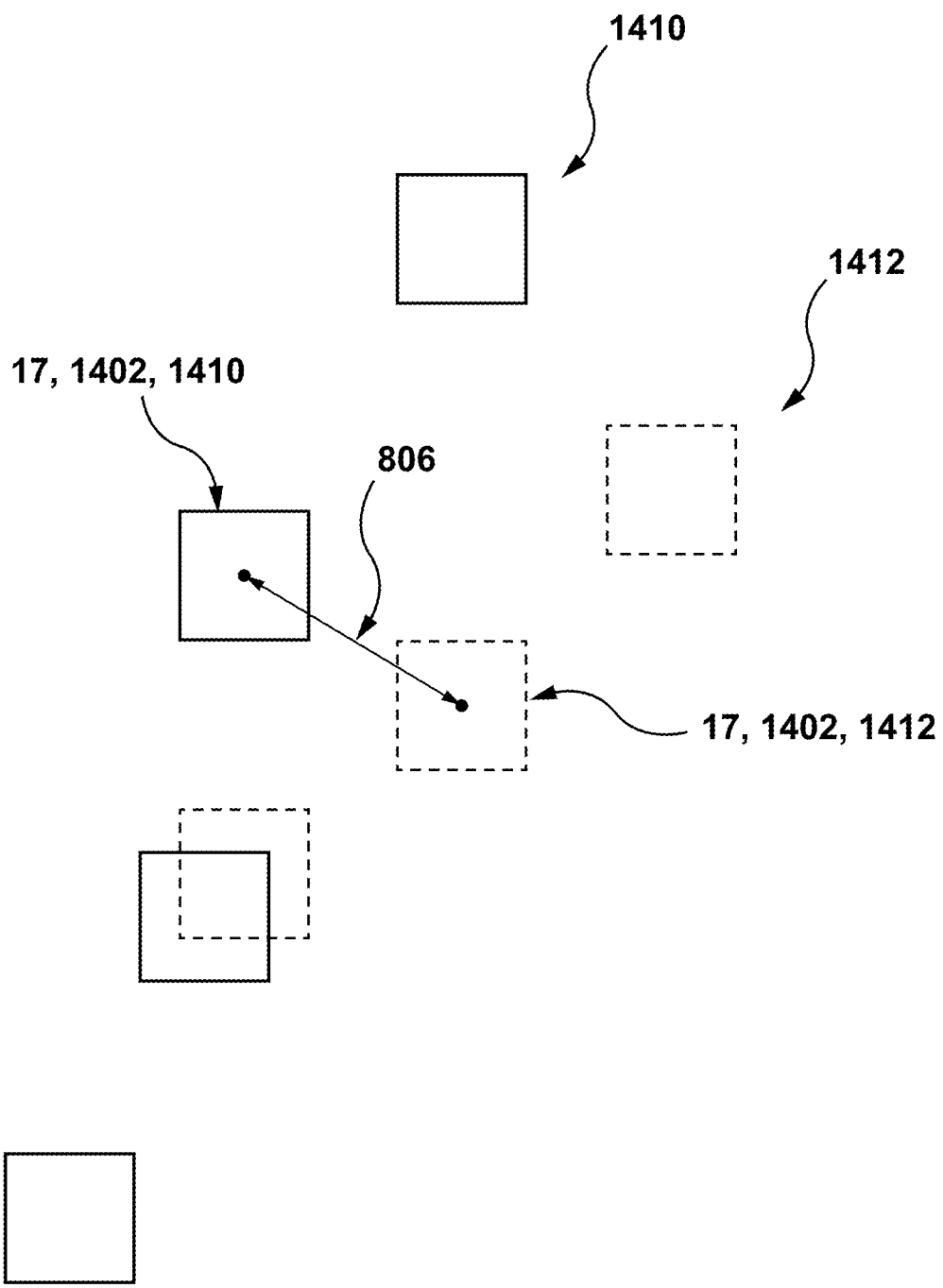
FIG. 15 depicts a schematic diagram of determining, based on the representations of the subject's teeth in the actual and planned positions thereof aligned as a whole, a deviation value between the actual and planned positions of the given tooth, in accordance with certain non-limiting embodiments of the present technology.

Thus, the processor 950 can be configured to iteratively execute the above steps until convergence of the RANSAC algorithm, thereby determining the alignment between the actual and planned distributions of 3D polygons 1410, 1412, which is representative of the alignment between the representations of the upper teeth 16, as a whole, in the actual and planned 3D digital models 1102, 1202. A magnified top view of the alignment between the actual and planned distributions of 3D polygons 1410, 1412, determined using the outlier detection algorithm is schematically depicted in FIG. 15, in accordance with certain non-limiting embodiments of the present technology.

Thus, as the respective primitive objects, such as the 3D polygons used in the example above, comprise simplified representations of the upper teeth 16 (compared to the original mesh representations thereof in the actual and planned 3D digital models 1102, 1202), the processor 950 can be configured to consume less computational resources for determining the alignment between the representations of the upper teeth 16 as a whole in the actual and planned 3D digital models 1102, 1202.

Further, based on this alignment between the actual and planned distribution of 3D polygons 1410, 1412 following the second alignment process described above, according to certain non-limiting embodiments of the present technology, the processor 950 can be configured to determine deviation values between the respective actual and planned positions of the upper teeth 16, as will be described below at step 1012.

However, in those non-limiting embodiments of the present technology, where each one of the actual and planned 3D digital models 1102, 1202 are respective point cloud 3D representations (not depicted) of the upper teeth 16 in the actual and planned positions, the processor 950 can be configured to execute the present step 1010 described above without preliminarily aligning the representations of the upper teeth 16 in the actual and planned 3D digital models 1102, 1202 individually as described at step 1008.

More specifically, the processor 950 can be configured to apply the outlier detection algorithm as described above directly to the respective point cloud 3D representations of the upper teeth 16 in the actual and planned positions thereof. At a greater level of granularity provided by the respective point cloud 3D representations, using the outlier detection algorithm as described above with respect to the actual and planned distributions of 3D polygons 1410, 1412, the processor 950 can be said to execute both the first and the second alignment processes with respect to the respective point cloud 3D representations at least partially concurrently, that is, (i) align portions of the respective point cloud 3D representations representative of individual ones of the upper teeth 16 relative each other; and (ii) align portions of the respective point cloud 3D representations representative of the upper teeth 16 as a whole.

Thus, in these embodiments, using the actual and planned 3D digital models 1102, 1202 comprising respective 3D point clouds representations, the processor 950 can be configured to determine the alignment therebetween without replacing the representations of upper teeth 16 with the respective primitive objects for using the outlier detection algorithm as described above. Further, the processor 950 can be configured to proceed to determining the deviation values between the actual and planned positions of each one of the upper teeth 16, as will be described immediately below.

The method 1000 hence advances to step 1012.

Step 1012: Determining, by the Processor, the Deviation Value Between the Actual and Planned Positions of the Given Tooth as a Deviation Value Between Positions of the Respective Primitive Object in the Actual and Planned 3D Digital Models of the Subject's Teeth Following the Second Alignment Process At step 1012, the processor 950 can be configured to determine the deviations values between the actual and planned positions of the upper teeth 16, such as the deviation value 806 between the respective actual and planned positions 802, 804 of the given tooth 17. With continued reference to FIG. 15, in some non-limiting embodiments of the present technology, the processor 950 can be configured to determine the deviation value 806 as a deviation value between the respective 3D polygon 1402 (or other types of the respective primitive objects mentioned above) representative of the given tooth 17 of the upper teeth 16 in the actual and planned distributions of 3D polygons 1410, 1412.

In those non-limiting embodiments of the present technology, where each one of the actual and planned 3D digital models 1102, 1202 are respective point cloud 3D representations of the upper teeth 16 in the actual and planned states, the processor 950 can be configured to determine the deviation value 806 as a distance between instances of the reference point associated with the given tooth 17 as described above with reference to FIG. 13, as an example.

Although in the embodiments depicted in FIG. 15, the deviation value 806 is determined in a projection of the actual and planned distribution of 3D polygons 1410, 1412 on a transverse (horizontal) anatomical plane associated with the subject, it should be expressly understood that, in other non-limiting embodiments of the present technology, the deviation value 806 can be determined in projections of the actual and planned distributions of 3D polygons 1410, 1412 on other anatomical planes associated with the subject, such as, a coronal (frontal) anatomical plane and/or sagittal (lateral) anatomical plane. Needless to mention, the deviation value 806 can be determined based on a mathematical combination (such as root of sum of squares, as an example) between the deviation values determined in at least two projections of the actual and planned distribution of 3D polygons 1410, 1412 on respective anatomical planes associated with the subject.

The method 1000 hence advances to step 1014.

Step 1014: In Response to the Deviation Value being Greater than a Predetermined Deviation Threshold, Adjusting the Tooth Trajectory of the Given Tooth to Minimize the Deviation Value Associated Therewith by an End of the Current Orthodontic Treatment Plan At step 1014, according to certain non-limiting embodiments of the present technology, the processor 950 can be configured to determine if the deviation value 806 associated with the given tooth 17 determined at step 1012 is sufficiently high for further correction thereof. To that end, in some non-limiting embodiments of the present technology, the processor 950 can be configured to determine if the deviation value 806 is greater than a predetermined deviation threshold, which can comprise, depending on a particular embodiment of the present technology, from 0.1 mm to 1.0 mm, as an example.

More specifically, in response to determining that the deviation value 806 is greater than a predetermined deviation threshold, the processor 950 can be configured to adjust the respective tooth trajectory 708 associated with the given tooth 17, determined as described above with reference to FIG. 7, such that from the given treatment step 714 onwards until the end of the current orthodontic treatment plan, the deviation value 806 is minimized, for example, to a predetermined minimum value.

According to certain non-limiting embodiments of the present technology, the processor 950 can be configured to adjust the respective tooth trajectory 708 by executing, from the given treatment step 714 onwards, at least one of: (i) increasing the respective force to be applied to the given tooth 17 along the movement segments of the respective tooth trajectory 708, such as the given movement segment 710, causing the given tooth 17 to move at longer distances during further treatment steps; and (ii) causing the given tooth 17 to move towards the desired position 44 along segments of the respective tooth trajectory 708 which were initially resting, such as the given resting segment 712. In other words, the processor 950 can be configured to re-determine those treatment steps of the plurality of treatment steps 706 of the current orthodontic treatment plan that begin from the given treatment step 714, while maintaining the total number of the treatment steps unchanged.

Figure 16:
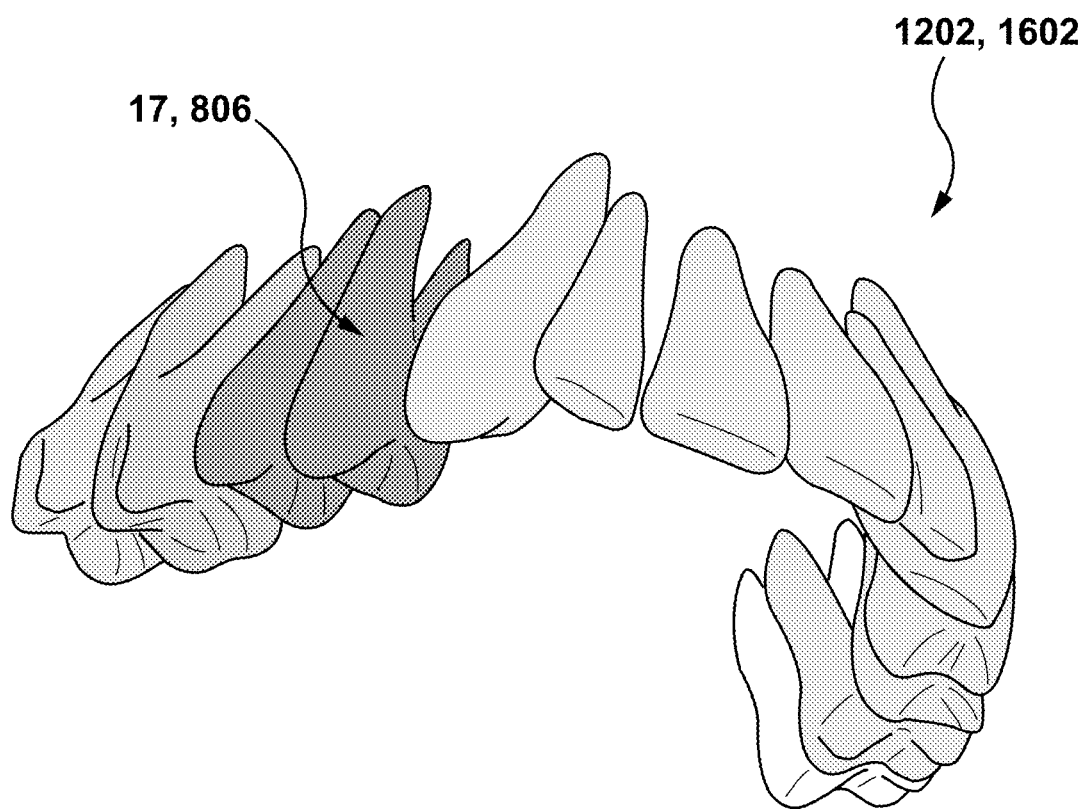
FIG. 16 depicts a schematic diagram of a heat map representative of deviation values between the actual and planned positions of the subject's teeth applied onto the planned 3D digital model of FIG. 12.

In additional non-limiting embodiments of the present technology, the processor 950 can be configured to visualize, for example, on the planned 3D digital model 1202, the deviation values determined for each tooth of the upper teeth 16, for example, in a form of a heat map representation 1602, schematically depicted in FIG. 16, in accordance with certain non-limiting embodiments of the present technology.

In some non-limiting embodiments of the present technology, the heat map representation 1602 may be a monochromatic heat map representation where greater deviation values associated with respective ones of the upper teeth 16 are assigned greater intensity values of a given color, and vice versa. In other non-limiting embodiments of the present technology, the heat map representation 1602 may be a polychromatic heat map representation (not depicted) associated with a predetermined color spectrum including at least two colors. In this example, the greater deviation values are assigned respective colors closer to a higher boundary of the predetermined color spectrum (being a red color, for example), and smaller deviation values are assigned colors closer a lower boundary (being a green color, for example) of the predetermined color spectrum.

Further, in some non-limiting embodiments of the present technology, the processor 950 can be configured to cause display of the planned 3D digital model with the heat map representation 1602 applied thereon, for example, on the screen 922 of the system 900. In additional non-limiting embodiments of the present technology, the processor 950 may be configured to store the heat map representation 1070 in one of the solid-state drive 960 and the random-access memory 970.

The method 1000 hence terminates.

Thus, certain embodiments of the method 1000 allow determining the deviation values between the actual and planned positions of the subject's teeth in a more efficient manner, using less computational resources of the processor 950, and further adjusting the current orthodontic treatment plan, thereby minimizing the so determined deviation value, without the need for generating a new orthodontic treatment plan. This may further allow saving time and resource costs of conducting orthodontic treatments.

It should be expressly understood that not all technical effects mentioned herein need to be enjoyed in each and every embodiment of the present technology.

Modifications and improvements to the above-described implementations of the present technology may become apparent to those skilled in the art. The foregoing description is intended to providing examples of implementations of the present technology rather than being limiting. The scope of the present technology is therefore intended to be limited solely by the scope of the appended claims.

The invention claimed is:

1. A method of adjusting a current orthodontic treatment plan having been previously determined for a subject, the current orthodontic treatment plan including an indication of a tooth trajectory of a given tooth towards a target position thereof, the adjusting comprising determining a deviation value between an actual position and a planned position of the given tooth of the subject at a given stage of the current orthodontic treatment plan, the method being executable by one or more processors, the method comprising:

acquiring, by the one or more processors, an actual 3D digital model including a representation of each one of the subject's teeth in actual positions thereof at the given stage of the current orthodontic treatment plan;

acquiring, by the one or more processors, an indication of the current orthodontic treatment plan;

generating, by the one or more processors, based on the current orthodontic treatment plan, a planned 3D digital model including a representation of each one of the subject's teeth in planned positions thereof at the given stage of the current orthodontic treatment plan;

aligning, by the one or more processors, during a first alignment process, each one of the subject's teeth in the actual 3D digital model and the planned 3D digital model individually, the aligning for the given tooth of the subject's teeth including:

matching (i) a respective representation of the given tooth in the actual 3D digital model with (ii) the respective representation of the given tooth in the planned 3D digital model;

aligning, by the one or more processors, during a second alignment process following the first alignment process, the subject's teeth in the actual 3D digital model and in the planned 3D digital model, as a whole, the aligning including:
obtaining, by the one or more processors, for each one of the subject's teeth, a respective primitive object of a plurality of representative objects;
replacing, by the one or more processors, each one of the subject's teeth in the actual and planned 3D digital models with the respective primitive object; and
determining, by the one or more processors, using an outlier detection algorithm, a matching between the plurality of representative objects, as a whole, in the actual and planned 3D digital models;
determining, by the one or more processors, the deviation value between the actual and planned positions of the given tooth as a deviation value between positions of the respective primitive object in the actual and planned 3D digital models of the subject's teeth following the second alignment process; and
in response to the deviation value between the actual and planned positions of the given tooth being greater than a predetermined deviation threshold, adjusting the tooth trajectory of the given tooth to minimize the deviation value between the actual and planned positions of the given tooth by an end of the current orthodontic treatment plan.

2. The method of claim 1, further comprising identifying the respective representations of the given tooth in the actual and planned 3D digital models based on an ordinal number of the given tooth within a respective arch form of the subject.

3. The method of claim 1, wherein the matching the respective representations of the given tooth in the actual and planned 3D digital models comprises:
merging, by the one or more processors, instances of a reference point associated with the given tooth in the respective representations thereof in the actual and planned 3D digital models.

4. The method of claim 3, wherein the reference point is a center of resistance associated with the given tooth.

5. The method of claim 3, wherein the reference point is one of a mesial point and a distal point associated with the given tooth.

6. The method of claim 3, wherein the reference point is a center point of a segmentation contour associated with the given tooth, indicative of a border between the given tooth and a gingiva of the subject.

7. The method of claim 3, wherein each one of the actual and planned 3D models comprises vertices representative of surfaces of the subject's teeth, and the matching further comprises:
applying, by the one or more processors, to the respective representations of the given tooth having been matched by merging the instances of the reference point therein, an alignment algorithm configured to determine correspondences between vertices of the respective representations of the given tooth in the actual and planned 3D digital model.

8. The method of claim 7, wherein the alignment algorithm is an iterative closest point (ICP) algorithm.

9. The method of claim 1, wherein each one of the actual and planned 3D models comprises vertices representative of surfaces of the subject's teeth, and the matching the respective representations of the given tooth in the actual and planned 3D digital models comprises:
during a first individual matching process, merging, by the one or more processors, instances of a reference point associated with the given tooth in the respective representations thereof in the actual and planned 3D digital models; and
during a second individual matching process, following the first individual matching process, applying, by the one or more processors, to the respective representations of the given tooth having been matched by merging the instances of the reference point therein, an alignment algorithm configured to determine correspondences between vertices of the respective representations of the given tooth in the actual and planned 3D digital model.

10. The method of claim 1, wherein the respective primitive object is a polygon.

11. The method of claim 10, wherein the polygon is a 2D polygon extending along an occlusal plane associated with the subject's teeth.

12. The method of claim 10, wherein the polygon is a 3D polygon.

13. The method of claim 12, wherein the 3D polygon is a bounding box defined around the given tooth.

14. The method of claim 1, wherein:
each one of the actual and planned 3D digital model comprises a respective 3D point cloud, the respective 3D point cloud comprising a respective plurality of points representative of surfaces of the subject's teeth in one of the actual and planned positions thereof at the given stage of the current orthodontic treatment plan;
the aligning during the first alignment process comprises determining, by the one or more processors, using the outlier detection algorithm, a matching between portions of the respective 3D point clouds representative of the given tooth in the actual and planned positions; and
the aligning during the second alignment process comprises determining, by the one or more processors, using the outlier detection algorithm, a matching between the respective 3D point clouds representative of the subject's teeth in the actual and planned positions as a whole.

15. The method of claim 1, wherein the outlier detection algorithm is a random sample consensus (RANSAC) algorithm.

16. The method of claim 1, wherein the adjusting the tooth trajectory is executed without changing a number of remaining stages of the current orthodontic treatment plan.

17. The method of claim 1, further comprising:
generating, by the one or more processors, along a surface of the actual 3D digital model, a heat map representative of deviation values associated with each one of the subject's teeth; and
causing, by the one or more processors, display of the heat map.

18. An electronic device for adjusting a current orthodontic treatment plan that has been previously determined for a subject, the current orthodontic treatment plan including an indication of a tooth trajectory of a given tooth towards a target position thereof, the adjusting comprising determining a deviation value between an actual position and a planned position of the given tooth of the subject at a given stage of the current orthodontic treatment plan;
the electronic device comprising at least one non-transitory computer-readable medium storing instructions; and at least one processor, which, upon executing the instructions, cause the electronic device to:

acquire an actual 3D digital model including a representation of each one of the subject's teeth in actual positions thereof at the given stage of the current orthodontic treatment plan;

acquire an indication of the current orthodontic treatment plan;

generate, based on the current orthodontic treatment plan, a planned 3D digital model including a representation of each one of the subject's teeth in planned positions thereof at the given stage of the current orthodontic treatment plan;

align, during a first alignment process, each one of the subject's teeth in the actual 3D digital model and in the planned 3D digital model individually, by:

matching (i) a respective representation of the given tooth in the actual 3D digital model with (ii) the respective representation of the given tooth in the planned 3D digital model;

align, during a second alignment process following the first alignment process, the subject's teeth in the actual 3D digital model and in the planned 3D digital model, as a whole, by:

obtaining, for each one of the subject's teeth, a respective primitive object of a plurality of representative objects;

replacing each one of the subject's teeth in the actual and planned 3D digital models with the respective primitive object; and determining, using an outlier detection algorithm, a matching between the plurality of representative objects, as a whole, in the actual and planned 3D digital models;

determine the deviation value between the actual and planned positions of the given tooth as a deviation value between positions of the respective primitive object in the actual and planned 3D digital models of the subject's teeth following the second alignment process; and in response to the deviation value between the actual and planned positions of the given tooth being greater than a predetermined deviation threshold, adjust the tooth trajectory of the given tooth to minimize the deviation value between the actual and planned positions of the given tooth by an end of the current orthodontic treatment plan.

19. A non-transitory computer-readable medium comprising a plurality of executable instructions for adjusting a current orthodontic treatment plan having been previously determined for a subject, the current orthodontic treatment plan including an indication of a tooth trajectory of a given tooth towards a target position thereof, the adjusting comprising determining a deviation value between an actual position and a planned position of the given tooth of the subject at a given stage of the current orthodontic treatment plan, wherein the executable instructions, when executed by at least one processor, cause the at least one processor to:

acquire an actual 3D digital model including a representation of each one of the subject's teeth in actual positions thereof at the given stage of the current orthodontic treatment plan;

acquire an indication of the current orthodontic treatment plan;

generate, based on the current orthodontic treatment plan, a planned 3D digital model including a representation of each one of the subject's teeth in planned positions thereof at the given stage of the current orthodontic treatment plan;

align, during a first alignment process, each one of the subject's teeth in the actual 3D digital model and in the planned 3D digital model individually, by:

matching (i) a respective representation of the given tooth in the actual 3D digital model with (ii) the respective representation of the given tooth in the planned 3D digital model;

align, during a second alignment process following the first alignment process, the subject's teeth in the actual 3D digital model and in the planned 3D digital model, as a whole, by:

obtaining, for each one of the subject's teeth, a respective primitive object of a plurality of representative objects;

replacing each one of the subject's teeth in the actual and planned 3D digital models with the respective primitive object; and determining, using an outlier detection algorithm, a matching between the plurality of representative objects, as a whole, in the actual and planned 3D digital models;

determine the deviation value between the actual and planned positions of the given tooth as a deviation value between positions of the respective primitive object in the actual and planned 3D digital models of the subject's teeth following the second alignment process; and in response to the deviation value between the actual and planned positions of the given tooth being greater than a predetermined deviation threshold, adjust the tooth trajectory of the given tooth to minimize the deviation value between the actual and planned positions of the given tooth by an end of the current orthodontic treatment plan.

20. The non-transitory computer-readable medium of claim 19, wherein the instructions that cause the at least one processor to match the respective representations of the given tooth in the actual and planned 3D digital models comprise instructions that cause the at least one processor to merge instances of a reference point associated with the given tooth in the respective representations thereof in the actual and planned 3D digital models, wherein the reference point is a center of resistance associated with the given tooth.

* * * * *